(12) United States Patent
Milo

(10) Patent No.: US 8,123,801 B2
(45) Date of Patent: Feb. 28, 2012

(54) IMPLANTATION SYSTEM FOR ANNULOPLASTY RINGS

(75) Inventor: Simcha Milo, Haifa (IL)

(73) Assignee: QuickRing Medical Technologies, Ltd., Haifa (IL)

( * ) Notice: Subject to any disclaimer, the term of this patent is extended or adjusted under 35 U.S.C. 154(b) by 603 days.

(21) Appl. No.: 12/364,414

(22) Filed: Feb. 2, 2009

(65) Prior Publication Data

US 2009/0177277 A1 Jul. 9, 2009

Related U.S. Application Data

(63) Continuation-in-part of application No. 10/873,703, filed on Jun. 21, 2004, now Pat. No. 7,485,142, which is a continuation-in-part of application No. PCT/IB02/05570, filed on Dec. 19, 2002.

(60) Provisional application No. 60/342,824, filed on Dec. 21, 2001.

(51) Int. Cl.
*A61F 2/24* (2006.01)
(52) U.S. Cl. ...................................... 623/2.11
(58) Field of Classification Search ................. 623/2.11, 623/2.36, 2.38, 2.39; 606/139, 142, 151, 606/213, 219, 228
See application file for complete search history.

(56) References Cited

U.S. PATENT DOCUMENTS

| | | |
|---|---|---|
| 4,217,665 A | 8/1980 | Bex |
| 4,917,698 A | 4/1990 | Carpentier et al. |
| 5,002,563 A | 3/1991 | Pyka et al. |
| 5,015,249 A | 5/1991 | Nakao et al. |
| 5,450,860 A | 9/1995 | O'Connor |
| 5,593,424 A | 1/1997 | Northrup, III |
| 5,674,280 A | 10/1997 | Davidson et al. |
| 5,709,695 A | 1/1998 | Northrup, III |
| 5,716,370 A | 2/1998 | Williamson, IV et al. |
| 5,843,178 A | 12/1998 | Vanney et al. |
| 5,961,539 A | 10/1999 | Northrup et al. |
| 5,972,004 A | 10/1999 | Williamson, IV et al. |

(Continued)

FOREIGN PATENT DOCUMENTS

WO  WO 01/87191 A1  11/2001

(Continued)

*Primary Examiner* — Kevin T Truong
(74) *Attorney, Agent, or Firm* — Fitch, Even, Tabin & Flannery, LLP

(57) ABSTRACT

Methods for reconfiguring an atrioventricular heart valve may use systems comprising a partial or complete fenestrated annuloplasty ring proportioned to reconfigure a heart valve that has become in some way incompetent, and a plurality of staples which may have pairs of legs that are sized and shaped for association with the ring at spaced locations along its length. These systems permit relative axial movement between the staples and the ring, whereby a patient's heart valve can be reconfigured in a manner that does not deter subtle shifting of the native valve components. Shape-memory alloy material staples may have legs with free ends that interlock following implantation. One alternative is to use flexible rings that will bend in the plane of the ring as the heart beats. Other alternative systems use linkers of shape-memory material having hooked ends to interengage with staples or other implanted supports which, following implantation, decrease in effective length and pull the staples or other supports toward one another so as to create desired curvature of the reconfigured valve. These linkers may be separate from the supports or may be integral with them and may have a variety of shapes and forms. Various of these systems may be implanted non-invasively using a delivery catheter.

10 Claims, 15 Drawing Sheets

U.S. PATENT DOCUMENTS

| | | |
|---|---|---|
| 6,001,127 A | 12/1999 | Schoon et al. |
| 6,007,577 A | 12/1999 | Vanney et al. |
| 6,042,607 A | 3/2000 | Williamson, IV et al. |
| 6,074,418 A | 6/2000 | Buchanan et al. |
| 6,096,074 A | 8/2000 | Pedros |
| 6,106,550 A | 8/2000 | Magovern et al. |
| 6,187,040 B1 | 2/2001 | Wright |
| 6,241,765 B1 | 6/2001 | Griffin et al. |
| 6,258,086 B1 | 7/2001 | Ashley et al. |
| 6,312,447 B1 | 11/2001 | Grimes |
| 6,322,548 B1 | 11/2001 | Payne et al. |
| 6,413,274 B1 | 7/2002 | Pedros |
| 6,524,338 B1 | 2/2003 | Gundry |
| 6,629,534 B1 | 10/2003 | St. Goar et al. |
| 6,752,813 B2 | 6/2004 | Goldfarb et al. |
| 6,986,775 B2 | 1/2006 | Morales et al. |
| 2011/0034953 A1* | 2/2011 | Milo .............................. 606/213 |
| 2011/0054598 A1* | 3/2011 | Johnson ....................... 623/2.39 |
| 2011/0106247 A1* | 5/2011 | Miller et al. ................. 623/2.36 |

FOREIGN PATENT DOCUMENTS

WO      WO 02/00099      1/2002

* cited by examiner

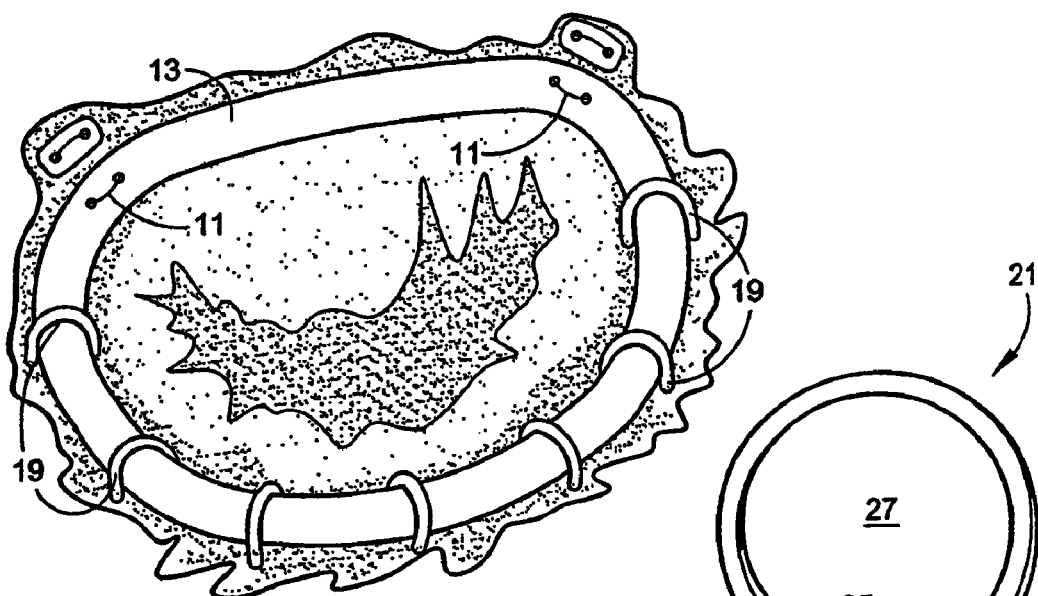
FIG. 4
FIG. 5
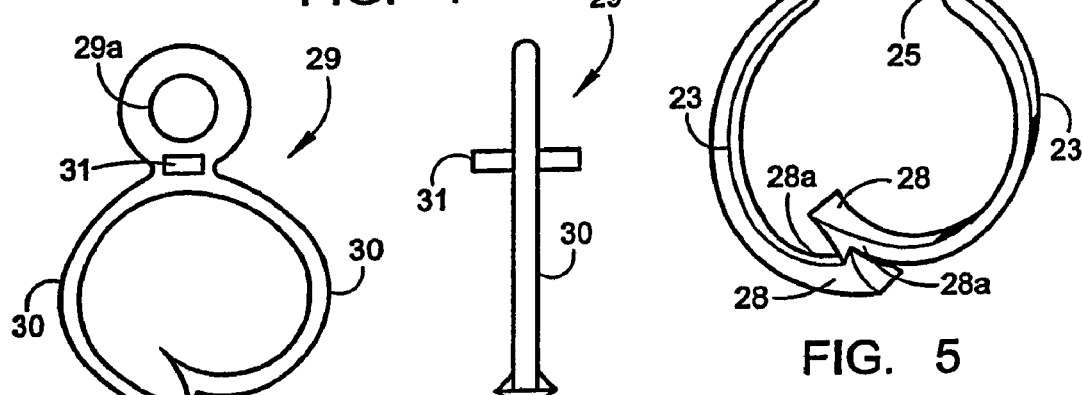
FIG. 5A   FIG. 5B
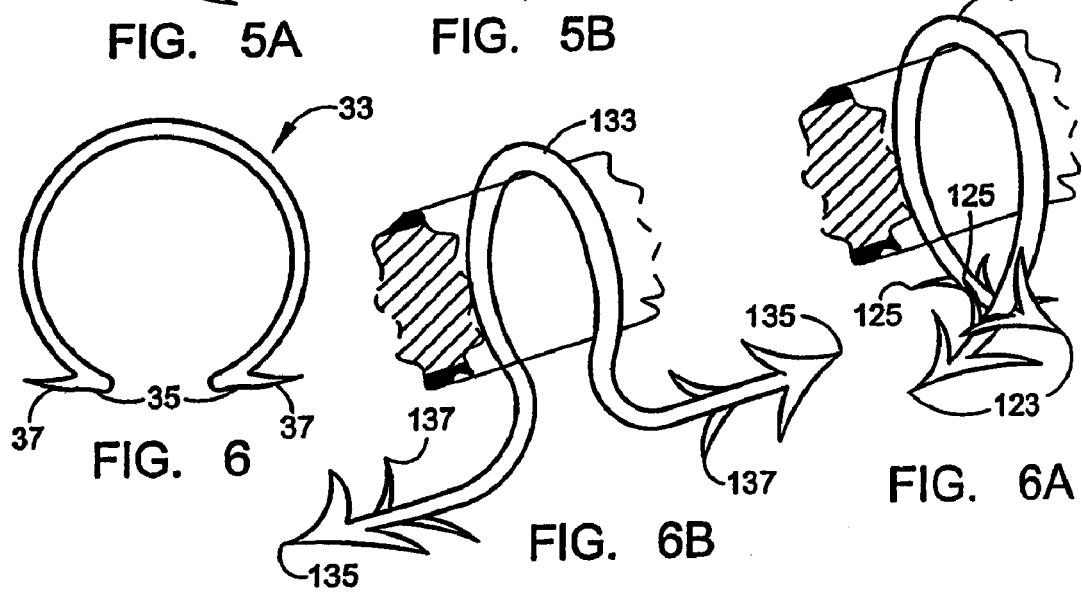
FIG. 6   FIG. 6B   FIG. 6A

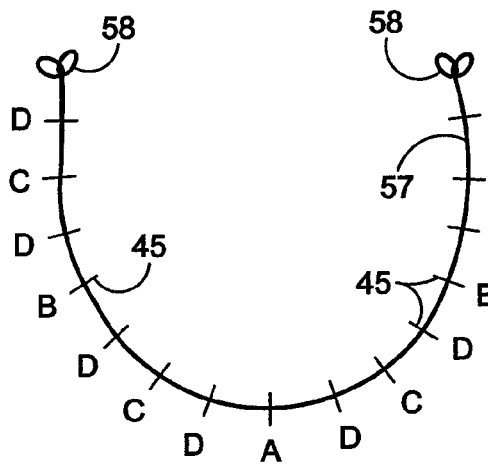
FIG. 11
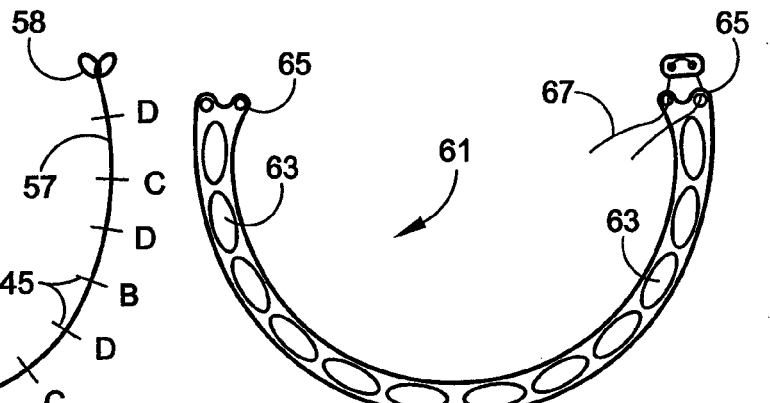
FIG. 12
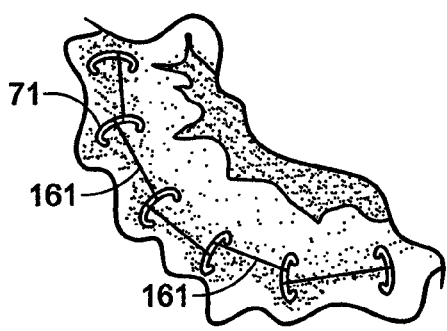
FIG. 14A
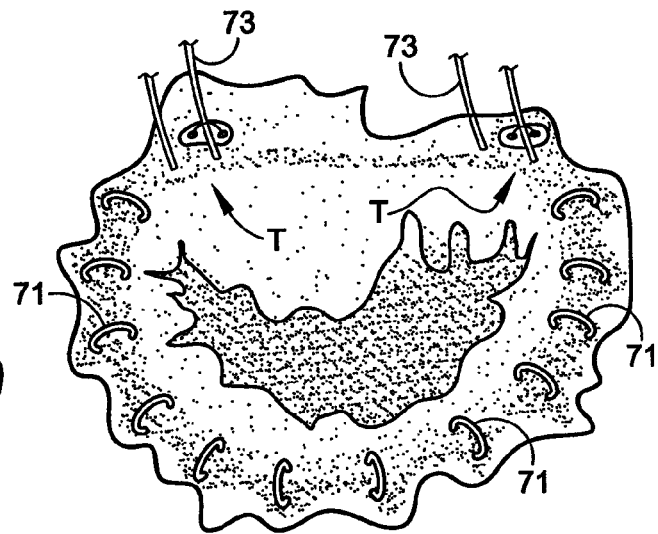
FIG. 14
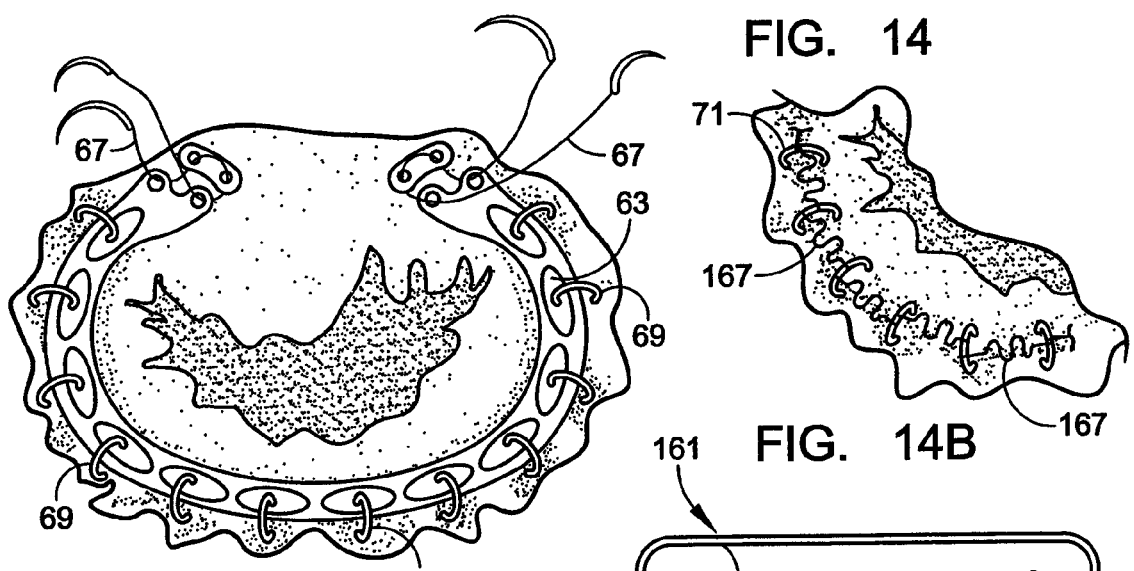
FIG. 13
FIG. 14B
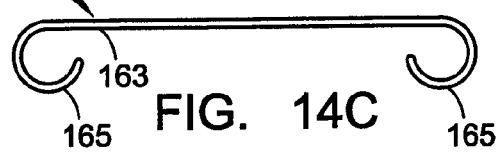
FIG. 14C

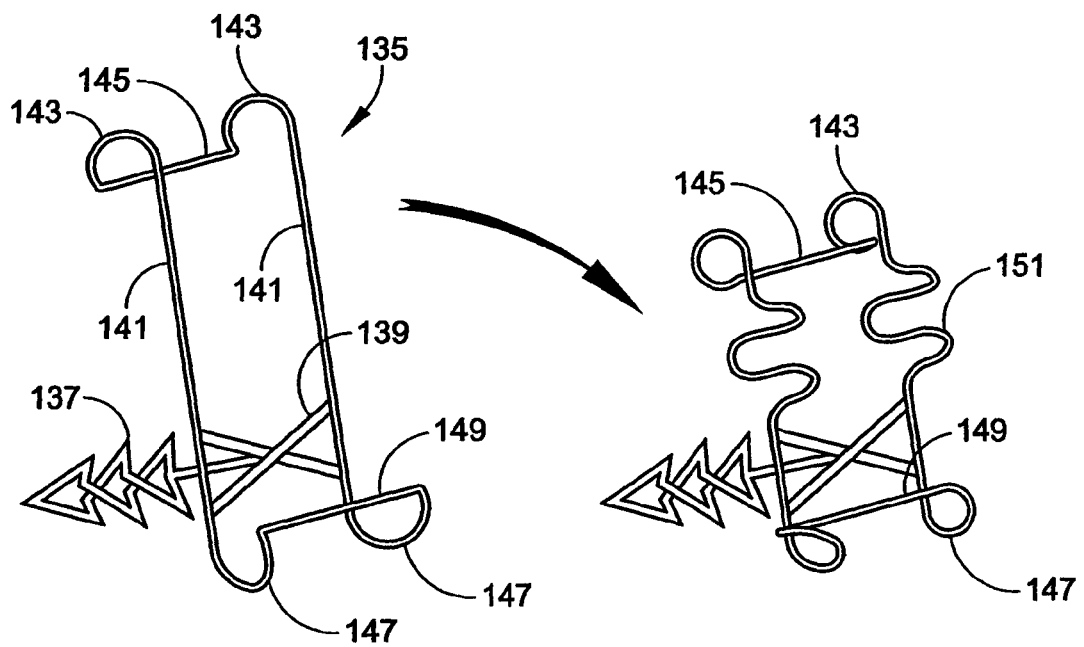
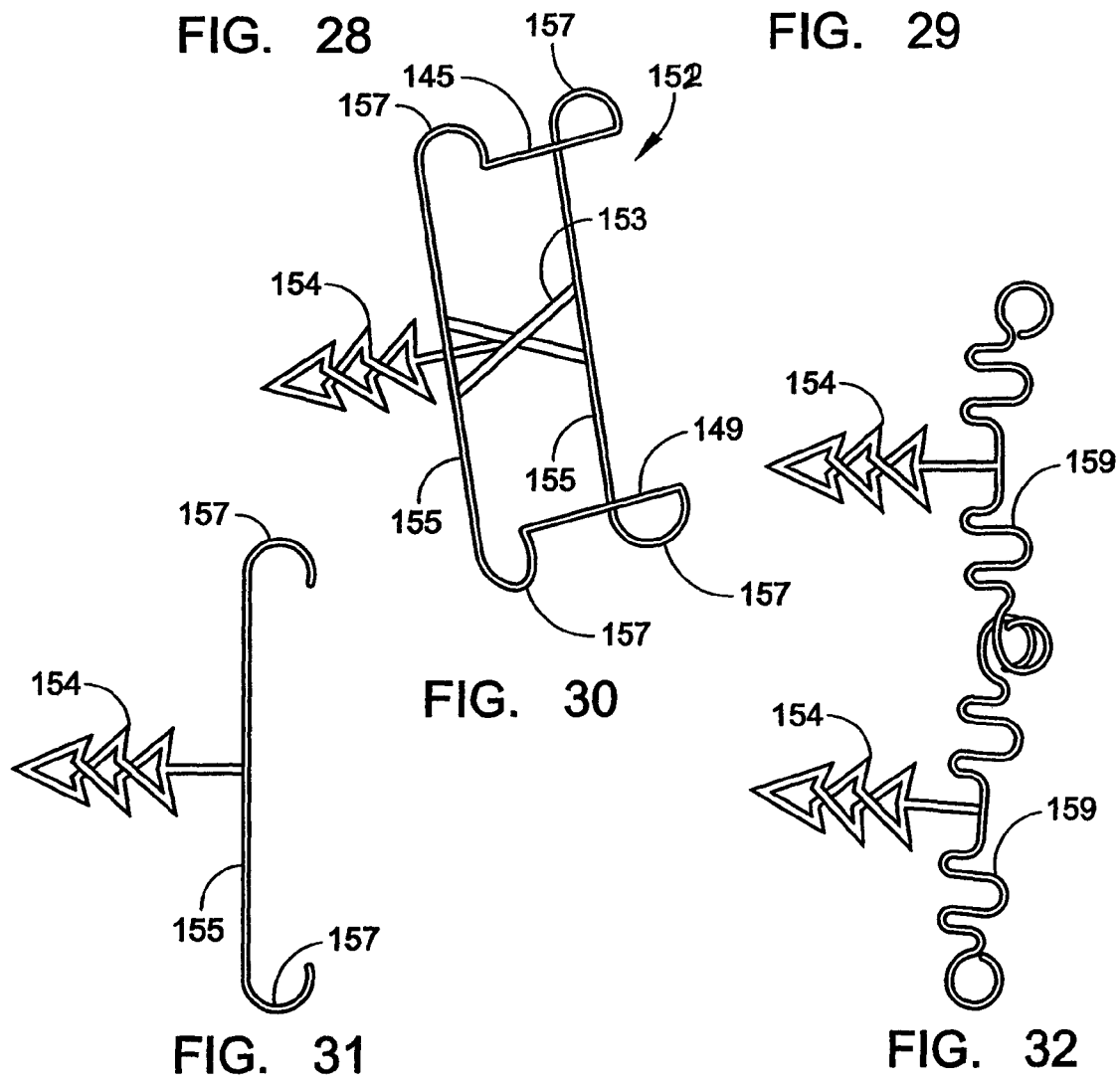

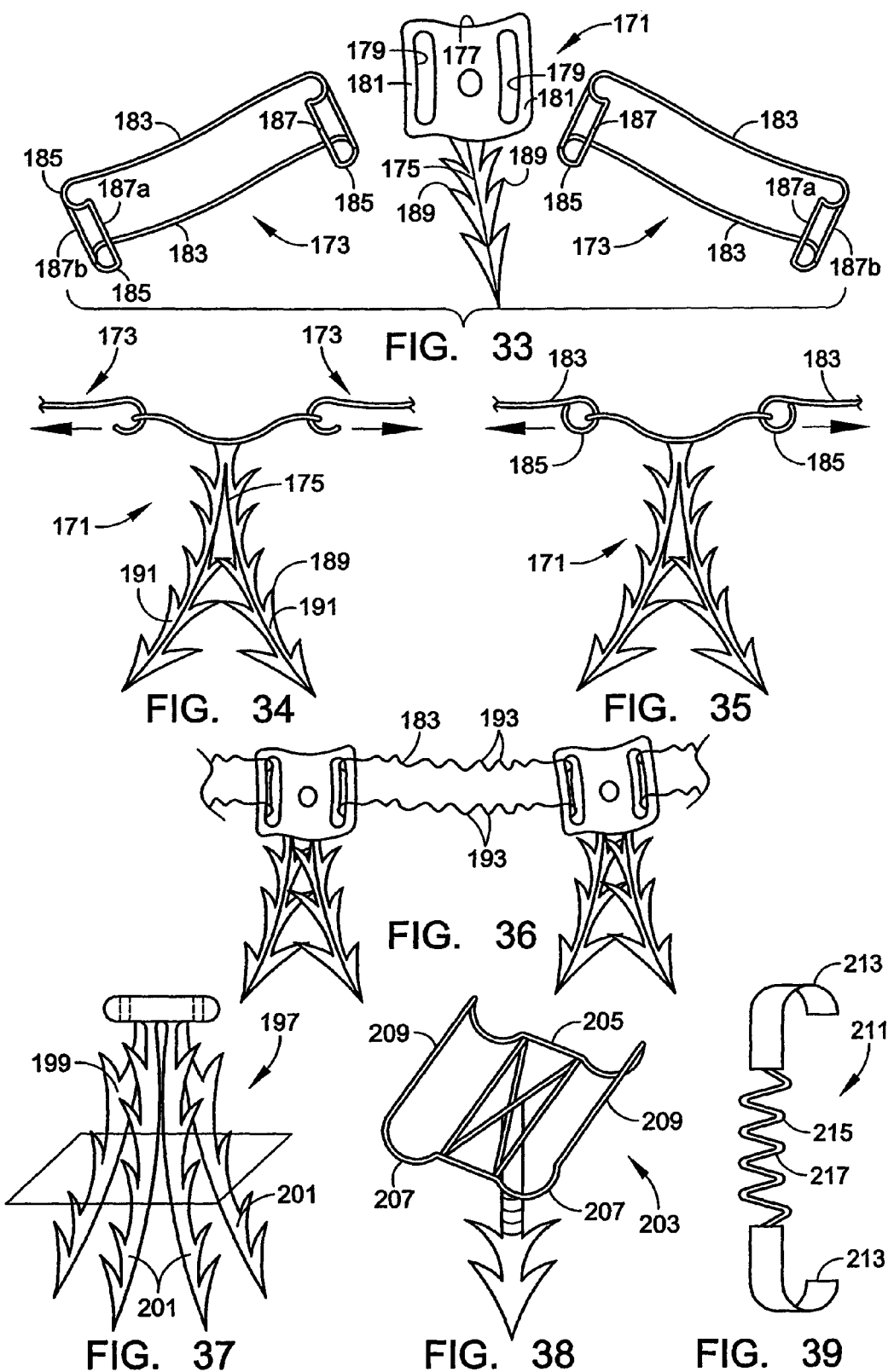

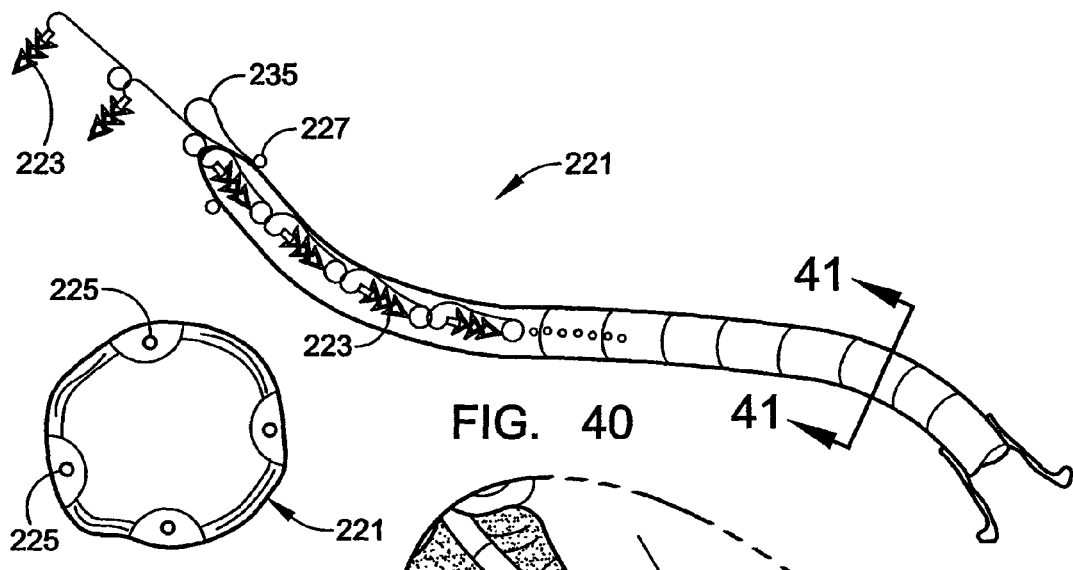
FIG. 40
FIG. 41
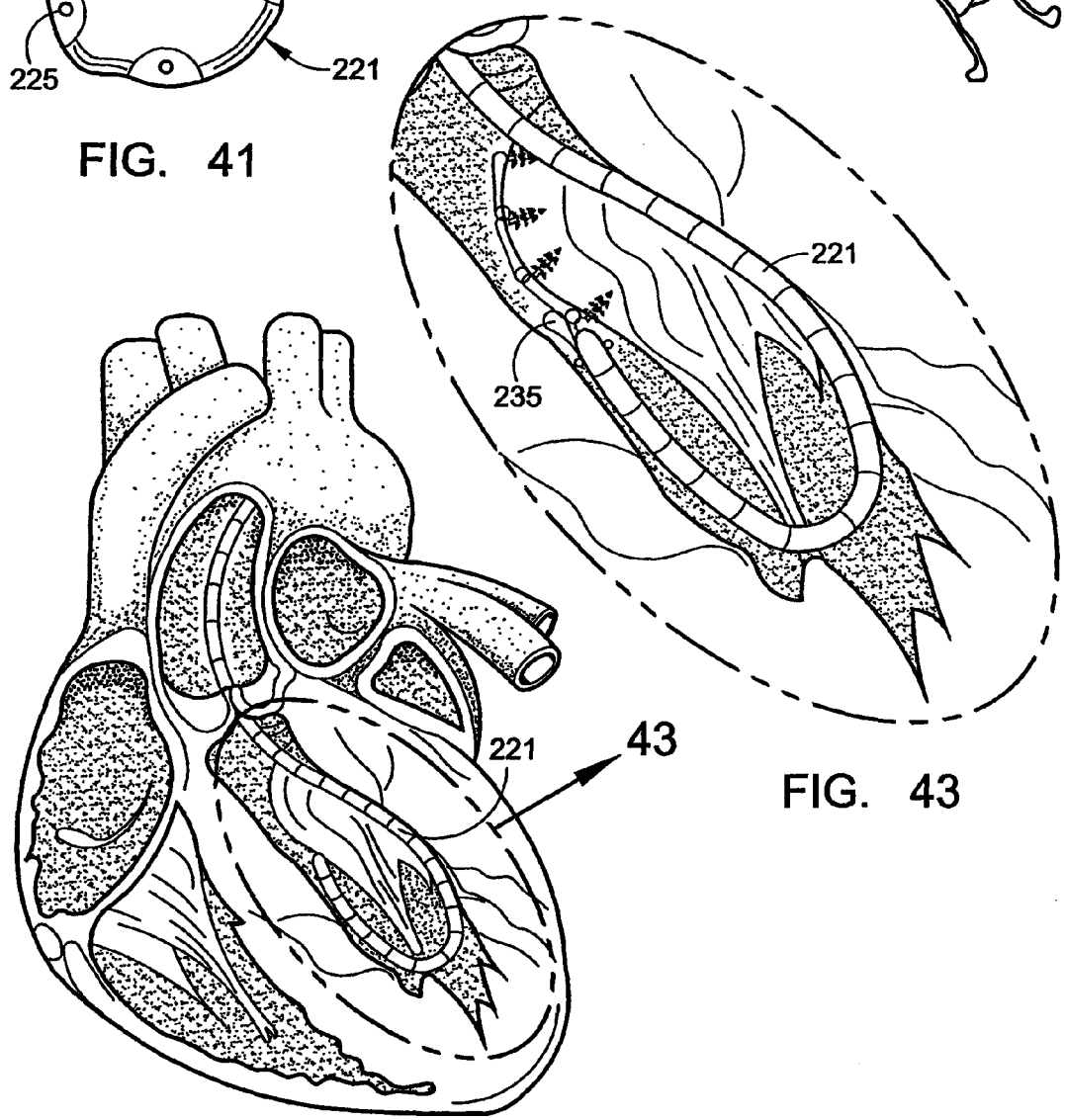
FIG. 43
FIG. 42

IMPLANTATION SYSTEM FOR ANNULOPLASTY RINGS

CROSS REFERENCE TO RELATED APPLICATIONS

This application is a continuation-in-part of U.S. Ser. No. 10/873,703, filed Jun. 21, 2004 which is a continuation-in-part of PCT/IB02/05570, filed Dec. 19, 2002, which claims priority from U.S. Provisional Application Ser. No. 60/342,824 filed Dec. 21, 2001. The disclosures of all three applications are incorporated herein by reference.

FIELD OF THE INVENTION

This invention relates to prosthetic annuloplasty ring systems designed to surgically correct defects in heart valves and more particularly to method and systems for the efficient and effective implantation of corrective rings and the like.

BACKGROUND OF THE INVENTION

Rheumatic, connective tissue or ischemic heart diseases may heavily affect the configuration of the atrioventricular heart valves. Diseased valves may become narrow, incompetent or both. A great many patients suffering from ischemic heart disease, who previously underwent myocardial infarctions, consequently develop various degrees of mitral valve incompetence. Typically in those patients, the valve may grossly seem to be normal; yet its annulus is dilated, causing coaptation or interengagement of the leaflets to be disturbed and resulting in incompetence of the valve. Such patients will benefit from an annuloplasty as a repair, either alone or in addition to a revascularization procedure, i.e. coronary artery bypass surgery. Most but not all mitral and tricuspid valves are amenable to reconstruction, and the etiology of valvular disease has an important bearing on the indication for repair. A rheumatic valve is probably the most difficult to conserve; conversely, degenerative valves with thin and redundant tissue, elongated or ruptured chordae, and/or a dilated annulus are very likely to be repairable. Ischemic regurgitation can often be repaired with annuloplasty.

Annuloplasty rings have now become essential components of reconstructive surgery of the mitral and tricuspid valves. Their safety and durability have been proven in numerous clinical studies that have occurred since their genesis in the late 1960's when Dr. Alain Carpentier introduced the prosthetic ring. This completely rigid ring had the systolic shape of the mitral and tricuspid valve; once sutured in place, the ring permanently stabilized the valve annulus into this shape. He designed a series of multi-sized fabric-covered rings with a stainless steel or a titanium core, which were configured to approximate the original shape of the diseased or dysfunctional valve annulus. Multiple sutures were sewn around the periphery of the annulus creating an entire circle of guide lines. The ring was positioned on the valve annulus, and the guide lines were then attached to the ring and used to draw the valve opening to the configuration of the ring (which would be the approximate shape of the original valve annulus). Although Dr. Carpenter's method could significantly improve valve function, some surgeons believe that the rigid structure of rings of this type may compromise the natural flexibility of the valve components. An open or partial ring annuloplasty prosthesis is described in U.S. Pat. No. 4,164,046; it discloses a uniquely shaped open ring useful for mitral and tricuspid annuloplasty having a special velour exterior.

Subsequent experimental and clinical echocardiographic studies showed that the mitral and tricuspid annuli change continuously in size and shape during the cardiac cycle. These results induced Dr. Carlos Duran, in 1975, to develop a completely flexible ring that could adapt to such changes. His fully flexible annuloplasty ring could only be shortened in the posterior segment by the placement of placating sutures; however, judgment of the position, size and spacing of these sutures requires skill and experience. Other adjustable annuloplasty rings are described in U.S. Pat. Nos. 4,042,979 and 4,290,151. Another type of flexible ring design is shown in U.S. Pat. No. 5,450,860 which includes an open ring in the form of a wide, flexible ligament that is implanted into the valve annulus. The ligament is typically made of expanded polytetrafluoroethylene to provide flexibility, promote tissue ingrowth and allow sutures to readily pass therethrough.

U.S. Pat. No. 6,524,338, issued Feb. 25, 2003, shows the stapling of a flexible, generally C-shaped band that fits over the prosterior valve annulus of a mitral valve while it is being held in place in the annulus by a positioning instrument to which it is releasably sutured. Staples stored in a magazine of a stapling device are individually fed from a delivery section at spaced locations along the outer periphery of the flexible band so as to attach outer regions of the band to the heart tissue.

In summary, the prevailing techniques that are now used throughout the world, without resorting to a full valve replacement, generally employ an annuloplasty ring to reduce a great part of the circumference of the valve. This is accomplished by suturing into place an elastic, semi-rigid or rigid ring that is smaller than the native annulus being reduced; the ring may be of a closed shape or an open band or C-shape. Installation takes place using regular sutures, in much the same manner as when a full valve replacement is carried out, and the procedure may consume as much time as a full valve replacement, for example, an average of about 35 to 45 minutes. Accordingly, improved annuloplasty systems and methods of reducing this time of surgery have continued to be sought.

SUMMARY OF THE INVENTION

The invention provides implantation systems and methods for implanting annuloplasty rings or the like which not only can be accomplished in a reduced time period but which are effective to achieve better coaptation of the leaflets following implantation. These systems result in improved hemodynamic functioning and substantially eliminate the risk of over-correction. Staples may be employed to affix a prosthesis to the patient's valve annulus in a manner to allow relative movement axially of the ring.

Certain such implantation systems may employ especially designed staples to implant an annuloplasty ring that may be of essentially any design, open or closed, generally replacing all the sutures previously used but the two trigonal sutures. Such staples can be delivered through a pistol-like applicator of the type generally used for surgical stapling to close wounds and the like. In one embodiment, such staples are initially implanted to provide a well-defined and easily installed pathway through which a flexible annuloplasty device can be routed and then ultimately secured in place by ligation to the two trigonal sutures. In other embodiments, staples or other supports are used to implant a ring or a partial or open ring of current design or to implant a fenestrated partial ring, that has been prepositioned in desired orientation on the patient's annulus. Further embodiments utilize specialized supports that have linkers of shape-memory material connected thereto, which linkers form a chain support following implantation. Some of these systems may be used to non-invasively reconfigure the mitral valve via a delivery catheter routed through the aortic valve into the left ventricle.

In one particular aspect, the invention provides a method of reconfiguring an atrioventricular heart valve, which method comprises providing an annuloplasty ring sized and shaped to have a desired configuration, and implanting said ring at the mitral or tricuspid valve of a patient by implanting a plurality of staples in the patient's heart tissue so as to spatially position said annuloplasty ring in a reconfiguration association therewith, while allowing the tissue in which said staples are implanted to have the ability to shift axially with respect to said ring.

In a further particular aspect, the invention provides a system for reconfiguring an atrioventricular heart valve, which system comprises a partial or complete annuloplasty ring having a size and shape proportioned to reconfigure a heart valve of a patient that has become in some way incompetent, a pair of pledgetted trigonal sutures, and a plurality of staples having pairs of legs that are sized and shaped for association with said ring at spaced locations along the length thereof in a manner that permits relative axial movement of said ring, whereby a patient's heart valve can be reconfigured in a manner that does not deter subtle shifting of the native valve components.

BRIEF DESCRIPTION OF THE DRAWINGS

FIG. 4 is a view similar to FIG. 3 showing the annuloplasty ring stapled in secure position.

FIGS. 5, 5A and 6 are front views of three different staples that might be employed to complete the implantation of the annuloplasty ring to the tissue of the patient.

FIG. 5B is a side view of the staple shown in FIG. 5A.

FIGS. 6A and 6B are perspective views of two additional styles of staples which might alternatively be used.

FIG. 11 is a plan view of a single wire partial annuloplasty ring schematically illustrating the preferred systematic placement of staples in association therewith.

FIG. 12 is a plan view of a fenestrated partial annuloplasty ring.

FIG. 13 is a view similar to FIG. 10 showing the fenestrated partial ring of FIG. 12 stapled in position with its ends ligated to the trigonal sutures.

FIG. 14 is a view similar to FIG. 1 of a mitral valve showing a pattern of staples implanted from commissure to commissure along a section of the native ring of the diseased mitral valve.

FIG. 14A is a fragmentary perspective view which shows an alternative embodiment to that illustrated in FIGS. 14-16, illustrating an alternative method of using the staple supports to a change a valve configuration.

FIG. 14B is a fragmentary perspective view similar to FIG. 14A showing the chain after the linkers have effectively shortened in length and thus pulled the staple supports closer to one another.

FIG. 14C is an elevation view of a linker seen in FIG. 14A.

FIG. 28 is perspective view of an alternative embodiment of a linker arm support of the general type shown in FIG. 24.

FIG. 29 is a perspective of the linker arm support of FIG. 28 after it has reverted to its original shape.

FIG. 30 is a perspective view of another alternative embodiment of a linker arm support similar to that shown in FIG. 28.

FIG. 31 is a front elevation view of the support shown in FIG. 30.

FIG. 32 is a schematic view showing two of the linker supports of FIGS. 30 and 31 after they have reached body temperature and reverted to their original shapes so as to schematically show the interengagement at one end between the respective linker arms of the two adjacent supports.

FIG. 33 is an exploded perspective view showing a further alternative embodiment of an implantation system for reconfiguring an atrioventricular heart valve having some similarities to that illustrated in FIGS. 30-32.

FIG. 34 is a fragmentary schematic view showing in elevation the implanted system of FIG. 33 after the anchor portion of the support has changed its shape.

FIG. 35 is a view similar to FIG. 34 showing the implanted system of FIG. 33 after the hook sections of the linkers have changed in shape to become essentially closed loops.

FIG. 36 is a perspective view of a portion of a chain of linkers and supports constructed from the elements of FIG. 33, showing the system after the arms have shortened in effective length.

FIG. 37 is a perspective view showing an alternative embodiment of a anchor portion of a central support similar to that as illustrated in FIG. 33 wherein there are four separate legs that spread radially at 90 angles to one another.

FIG. 38 is a perspective view of another alternative embodiment of a central support that could be substituted for that shown in FIG. 33 wherein the base is of generally wire form.

FIG. 39 is a perspective view of an alternative embodiment of a linker to that shown in FIG. 36, showing it after it has returned to its original shape.

FIG. 40 is a schematic view showing a delivery catheter holding a chain of interconnected supports designed for use in non-invasively shortening the circumstance of a mitral valve.

FIG. 41 is a cross sectional view through a section of the delivery catheter taken generally along the line 41-41 of FIG. 40.

FIG. 42 is a schematic view showing the delivery catheter inserted into the left ventricle through the aortic valve as it is being positioned to forcefully insert a row of interlinked supports into the heart tissue.

FIG. 43 is a fragmentary view showing an initial portion of the chain of interlinked supports in place along the annulus of the mitral valve as the delivery catheter is being moved along the path to insert them one at a time.

DETAILED DESCRIPTION OF THE PREFERRED EMBODIMENTS

It has been found that, through the use of supports, such as staples and preferably staples of a preferred design, an improved annuloplasty system can be created that can be installed, for example, with the use of only two U-shaped, pledgetted trigonal sutures, in less than one-half the time it presently takes to install the present generation of annuloplasty rings. For purposes of this application, the term "annuloplasty ring" is intended to include complete generally D-shaped rings as well as open rings or bands that may have a generally C-shape and which are rigid or flexible; in any event, an annuloplasty ring system which is used will be proportioned so as to reconfigure an atrioventricular heart valve that has become incompetent or in some other way defective. Heretofore, the incorporation of an annuloplasty ring has involved an operation that generally required about as much time in surgery as an actual total valve replacement. However, using the present invention, this time can be reduced by 50% or more, thus substantially shortening the time when the patient need be on artificial life support and making surgeons more willing to use an annuloplasty procedure whenever felt feasible. Installation using certain embodiments of the invention can be carried out by first positioning an annuloplasty ring in association with the annulus of the valve to be reconfigured and then applying staples, or alternatively by first implanting a series of spaced apart supports, such as staples along the valve annulus to create a desired pathway for an annuloplasty ring of open configuration and then routing such a ring through portals provided by the supports defining such pathway. Methods of implantation where a ring is first juxtaposed with the heart tissue are first described, followed by other manners of implantation.

Figure 1:
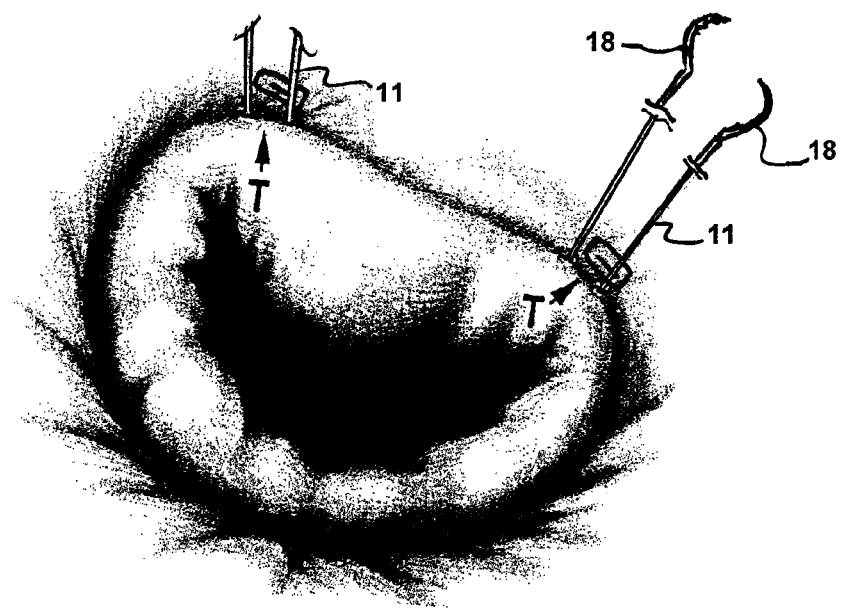
FIG. 1 is a top perspective view showing a mitral valve with a pair of trigonal sutures extending from the commissures thereof.
Figure 2:
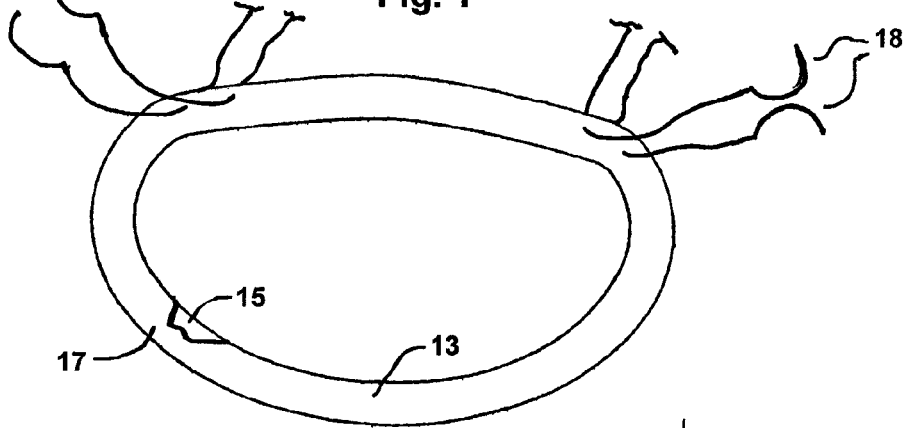
FIG. 2 is a plan view of an annuloplasty ring that might be associated with the valve of FIG. 1 to reconfigure it.
Figure 3:
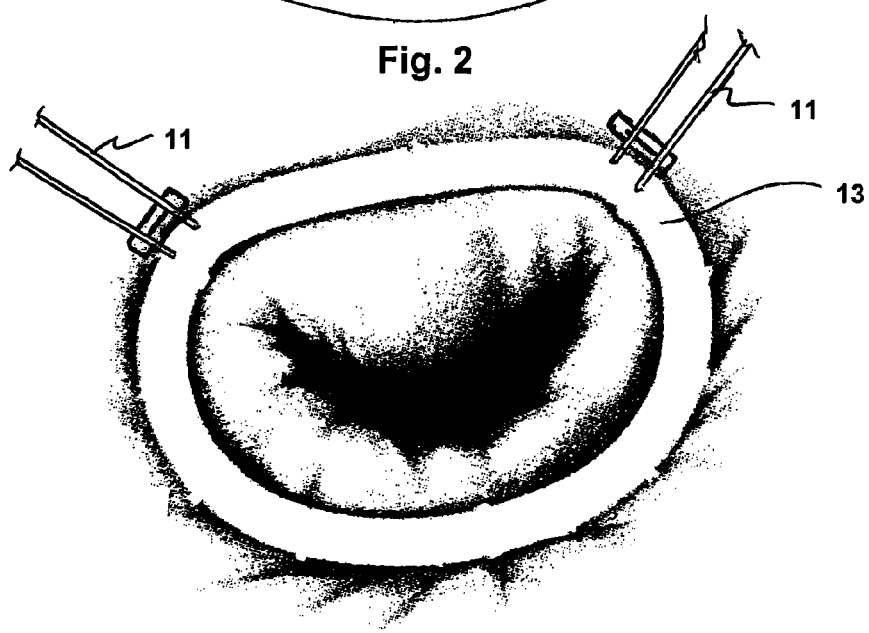
FIG. 3 is a perspective view similar to FIG. 1 with the annuloplasty ring similar to that shown in FIG. 2 located in desired association with the native annulus of the patient's valve, with the two trigonal sutures extending through a fabric covering of the ring.

FIG. 1 shows a mitral valve having a pair of trigonal pledgetted sutures 11 extending from the commissures thereof. Pledgetted sutures which are placed at the respective commissures act both as markers which position the annuloplasty ring, and as tie-down sutures that are ligated at the completion of the implantation operation. Such are the only two sutures that are employed in implanting a closed annuloplasty ring such as the ring B shown in FIG. 2. The ring 13 has a core 15 that is suitably covered. The core 15 may be solid or may contain a coiled helical spring or the like as known in this art, if a flexible ring is desired. The ring 13 is of generally circular cross section; however, rings of different cross sections may be employed as described hereinafter. The core may be covered with a thin layer 17 of a biocompatible fabric, such as woven polyester, which fabric may optionally be associated with expanded polytetrafluoroethylene sheet material. Suture needles 18 at the opposite ends of the trigonal sutures 11 are threaded through the fabric 17 as shown in FIG. 3. The sutures are later ligated once the ring has been secured in place by attachment to the valve annulus via staples. After gauging the valve to select the proper size ring 13, the annuloplasty ring is located in association with the native annulus of the patient's valve as shown in FIG. 3, with the two trigonal sutures 11 extending through the fabric covering 17 of the ring.

Once the annuloplasty ring is positioned in contact with the annulus ring of the mitral valve to be reconfigured, it is quickly secured in the exact desired position by the implantation of staples 19, (see FIG. 4); the staples in this embodiment are individually secured to the valve tissue at spaced apart locations about the entire length of the ring so as to spatially secure it radially while allowing the tissue to move axially of the ring. Surgical staples having a pair of legs may be implanted using any suitable commercially available surgical stapler of which there are quite a variety being marketed today. Examples of such staplers include those shown in U.S. Pat. Nos. 5,782,397 and 5,918,791.

Once about 7-10 spaced-apart staples 19, which may be of any, suitable design, have been applied about the ring 13 along its entire length to secure the ring radially about the valve, as shown in FIG. 4, the two trigonal pledgetted sutures 11 are ligated to the annuloplasty ring. Ligation completes the implantation, and the entire operation will take less than one-half the time it takes to presently install a similar annuloplasty ring using a myriad of sutures as is currently common practice.

Although a variety of staples may be employed as generally known in the surgical stapling art, certain preferred staples are illustrated hereinafter. FIG. 5 illustrates a staple 21 having a pair of legs 23 that are formed with two inwardly protruding, opposed bends 25 which are located at the tissue surface. In their operative orientation, the legs create a portal 27 that will be located above the surface of the tissue to which the annuloplasty ring is being secured. The staple 21 will preferably reasonably closely surround the ring 13, which may be of circular cross-section, so as to effectively restrain it against movement in a radial direction while allowing free relative movement of the staple (and thus the valve tissue) along the length of the ring. Free ends 28 of the two legs 23 of the staples are customarily pointed, and they may be originally or subsequently curved at the time of implantation so as to secure the staples in the tissue. Preferably, the staples 21 are made of a shape-memory material, such as taught in U.S. Pat. No. 4,485,816, the disclosure of which is incorporated herein by reference; for example, they may be made of Nitinol, a metal alloy material. For example, the staples may be originally formed in their desired closed shape and subsequently cooled below a transition temperature before deforming them into an open shape. It is conceivable that other types of shape-memory material might be used which would regain an initial configuration following implantation after treatment with energy, e.g., UV radiation or the like. After placement in the valve tissue, the staples 21 will revert to their original closed shape, and they will be capable of generating sufficient stress to penetrate through the tissue in which they reside so that the free ends 28 assume a secure orientation. More preferably, the free ends 28 of the staples are formed so as to interlock with each other, as by providing interlocking barbs 28a, and such interlocking can be designed to occur as a result of the shape-memory material reverting to its originally formed shape. Most preferably, the staples 21 are formed of a metal material having legs 23 with flat surfaces of a substantial width. Barbs 28a protrude from facing surfaces, and the legs are designed so that the free ends will overlap each other, preferably one above the other so that the interlocking of the barbs will occur in the plane of the staple 21 itself.

FIG. 5A shows a generally similar staple 29 which might be preferred when staples are to be first implanted in spaced apart locations along the valve annulus to create a desired pathway for an annuloplasty ring of open configuration, as described hereinafter. The staple 29 has a closed upper ring section 29a that is appropriately sized to provide an opening to which an annuloplasty ring might be attached, as described hereinafter. The ring surmounts a pair of curved legs 30 which terminate in free ends similar to the barbed free ends 28 of the staples 21. To positively prevent the staple from being driven too deeply into the tissue, a pair of oppositely extending wings 31 are provided which extend transversely outward preferably perpendicular to the plane of the staple, as best seen in FIG. 5B. The wings will engage the surface of the tissue and limit the depth of implantation of the staple to that desired. Implantation of the staples 29 would be generally similar to that of the staples 21 described above.

In the embodiment shown in FIG. 6, a staple 33 of simpler configuration is shown. The staple 33 is generally circular in shape, so proportioned to surround the perimeter of a circular cross-section annuloplasty ring, and its two spaced-apart free ends 35 are formed with barbs 37 of the type commonly found at the end of a standard fish hook. Accordingly, these staples 33 can be readily implanted using a surgical stapler of the type commonly employed; they need not be made of a shape-memory material, as they can be essentially clinched in place by standard stapling action.

Two additional staple designs having advantageous features are illustrated in perspective views labeled FIGS. 6A and 6B. Illustrated in FIG. 6A is a staple design 121 which generally resembles staple 21 without the two interior bends 25. The staple has two free ends 123, which carry laterally extending barbs 125. The staples 121 would be similarly placed, so that the annuloplasty ring would reside in the bight of the staple and the free ends would cross. As a result of the design, the laterally extending barbs 125 would interengage, thus locking the staples in place, with the barbs embedded in the heart tissue. The staples could be made of a shape-memory material, or they could be made of a high grade stainless steel or the like and crimped by a suitable surgical stapling tool. Illustrated in FIG. 6B is a staple 133 that generally resembles staple 33. The staple similarly has a pair of spaced apart free ends 135 that are formed with barbs 137. In this arrangement, the staples 133 are similarly placed so that the annuloplasty ring resides in the bight of the staple, but in this arrangement, one free end 135 extends in one direction and the other free end extends in the essentially opposite direction, both which directions are essentially parallel to the axis of this section of the annuloplasty ring. Again, the staples 133 can be formed from a shape-memory material, which will then inherently assume this orientation, or they may be made of stainless steel or the like and implanted using a tool which causes this particular deflection of the respective free ends.

Figure 7:
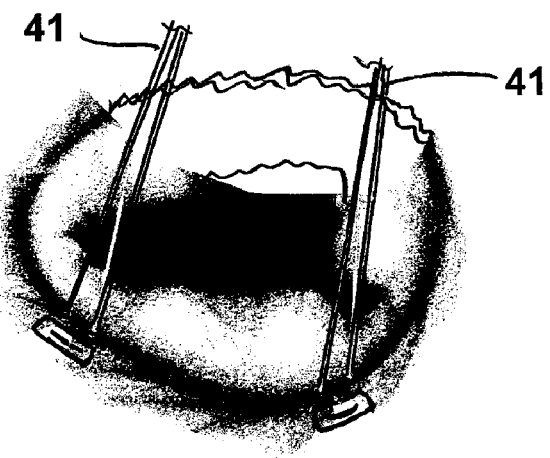
FIG. 7 is a view similar to FIG. 1 showing a tricuspid valve with two trigonal sutures in place.
Figure 8:
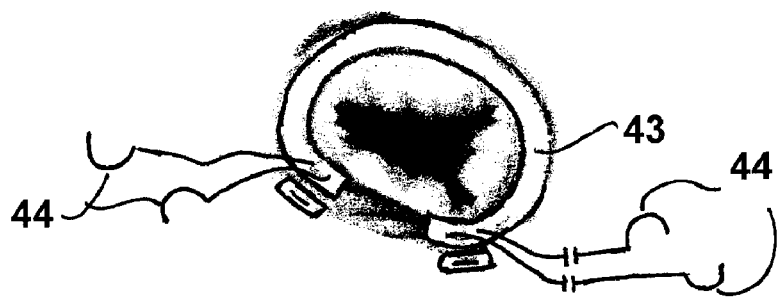
FIG. 8 is a view similar to FIG. 3 with a flexible annuloplasty partial ring associated with the valve of FIG. 7.
Figure 9:
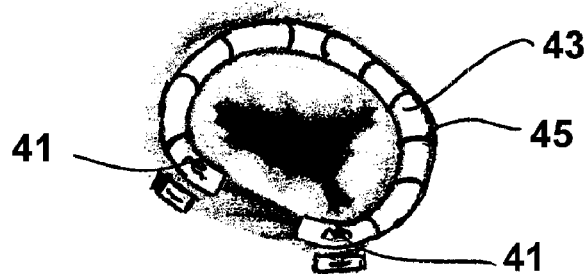
FIG. 9 is a view similar to FIG. 8 showing the partial annuloplasty ring stapled into place with the trigonal sutures ligated thereto.

The implantation of a partial annuloplasty ring or band in conjunction with a tricuspid valve is illustrated and described with respect to FIGS. 7-9. In FIG. 7, a tricuspid valve is shown with two double-armed 2.0 pledgetted sutures 41 pulled for retraction. The tricuspid valve to be reconfigured is gauged, and the size of a partial ring 43 desired is determined. The two trigonal sutures 41 are then sutured to the ring 43 at the appropriate sites using suture needles 44 integrally attached to the ends thereof, and the ring 43 is lowered into association with the annulus of the valve as shown in FIG. 8. Staples 45 as described hereinbefore are radially placed around the annulus in the sequence illustrated in FIG. 11, the sequence of placement being indicated alphabetically, starting with "A". More specifically, a staple 45 is first placed at the midpoint of the ring, and then two staples 45 are placed halfway between the midpoint and each end at the "B" locations. Thereafter, additional staples 45 are placed equidistant between pairs of existing staples or between the end of the ring and the nearest staple, in two separate series, i.e. "C" and then "D", until the illustrated pattern is achieved. By placing the staples 45 in such a sequence, maximal anchoring symmetry is obtained which results in maximal coaptation of the leaflets and competent valve operation. Once all of the staples 45 are in place, both trigone anchoring sutures 41 are ligated, as depicted in FIG. 9. As should be apparent, this simplified procedure can be completed in a fraction of the time needed for traditional annuloplasty ring implantation. As a result of the procedure, the incompetent valve has been effectively reconfigured while subtle relative movement is still permitted between the stapled tissue and the annuloplasty ring in a direction axial of the ring, assuring excellent interengagement of the leaflets.

Figure 10:
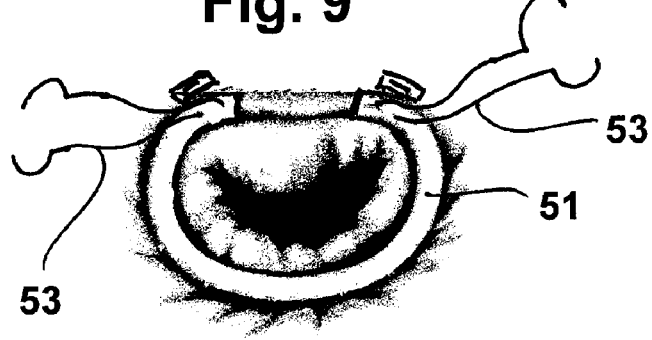
FIG. 10 is a view similar to FIG. 1 showing a mitral valve with a partial annuloplasty ring in place and with the ends thereof associated with the trigonal sutures.

FIG. 10 illustrates a mitral valve with a partial annuloplasty ring 51 in place, similar to the one described with regard to the tricuspid valve. The pledgetted trigonal sutures 53 will be ligated to the ends of the generally C-shaped ring 51, as described hereinbefore, following placement of the confining staples 55.

FIG. 11 shows an alternative type of single wire partial annuloplasty ring 57 in combination with a pattern of staples to which reference was earlier made to describe the strategic sequential placement of staples 45 about an annulus. These staples 45 can be implanted in locations straddling the wire, or staples 29 might be used having openings in the ring sections such that the wire may be passed therethrough. Instead of attaching trigonal sutures to a fabric covering as was previously described with respect to other such rings, the single wire partial annuloplasty ring 57 is provided with a pair of ears 58 at each end which are preferably be apertured to facilitate the ligation of the trigonal sutures thereto after they are threaded therethrough. The "A" staple is placed first, followed by the two "B" staples, followed by the four "C" staples, etc.

Illustrated in FIG. 12 is a fenestrated partial annuloplasty ring 61 made of a suitable metal alloy material, e.g. titanium or Nitinol. The generally C-shaped partial ring 61 has a plurality of elongated windows 63 running down its spine for its entire length, and a pair of apertured ears 65 are provided at each end to facilitate attachment of trigonal sutures 67 thereto. The windows 63 are proportioned so that a staple 69 can be located generally at the midpoint of each window, with one leg of the staple protruding through the window and with the staple preferably straddling the radially outer edge of the fenestrated, ring as illustrated in FIG. 13. The ring 61 can be flat, but it may advantageously be frustoconical, being disposed at an angle of about 10° to about 60° (and preferably between about 10° to about 45°) to the horizontal (i.e. to the plane which is perpendicular to the axis of the valve). Either the smaller or the larger diameter edge may be implanted closest to the valve opening, as there is great variation in the mitral valves of different patients. With the mitral valve reconstruction shown in FIG. 13, the larger diameter radially outer edge faces the valve opening. Once all of the desired staples 69 are in place, generally one with respect to each window, the pledgetted trigonal sutures 67 are ligated to the attachment ears 65 at the respective ends of the partial ring. As can be seen, the elongated windows 63 allow free relative axial movement between the edge of the fenestrated band and the staples, which are secured in the heart valve tissue. Again, the staples 69 can be any of the types depicted in FIGS. 5, 6, 6A and 6B, or they can be of the general surgical variety as it is unnecessary for them to provide a defined portal or bight-shaped to particularly surround the circumference of a circular cross-section band.

As indicated, the annuloplasty ring 61 might be made of a suitable metal alloy, and depending upon the thickness of the metal alloy from which the fenestrated ring is made, it could be essentially rigid (relative to the heart valve tissue to which it would be stapled) or it could exhibit some flexibility. It may be desirable for annuloplasty rings to be designed to more closely comply with the individual anatomical configurations of the heart valve of a particular person being repaired, and by providing a ring which will flex with and follow the physiologic cyclical movements of the valve tissue, the adjustments to the valve effected by the ring will disturb the leaflets as little as possible and thereby facilitate the valve regaining its optimal function. Shown in FIGS. 44-49 are a number of alternative embodiments of annuloplasty rings, similar to the ring 61, which could be constructed of a material so as to be either relatively rigid, as compared to the heart valve tissue surface to which it would be secured, or pliable.

Figure 15:
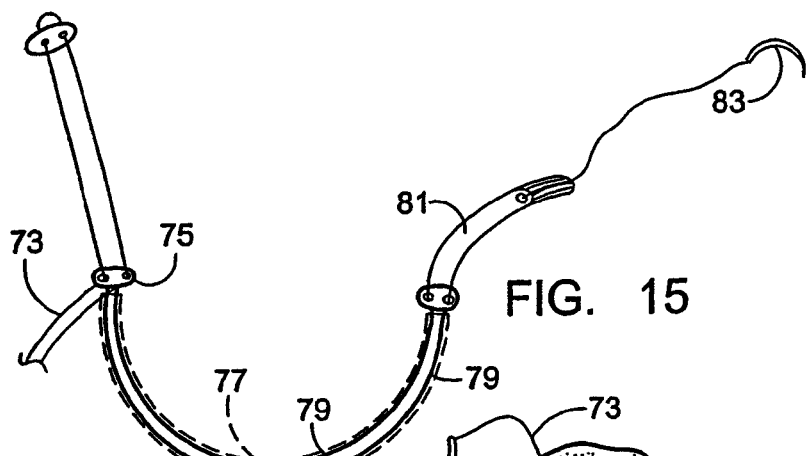
FIG. 15 is a schematic view showing a needle attached to the lead end of a flexible annuloplasty band disposed in a sheath and ready to be routed from one commissure to the other through the pattern of implanted staples, with the tail band being shown connected to the ends of the left-hand trigonal suture.
Figure 16:
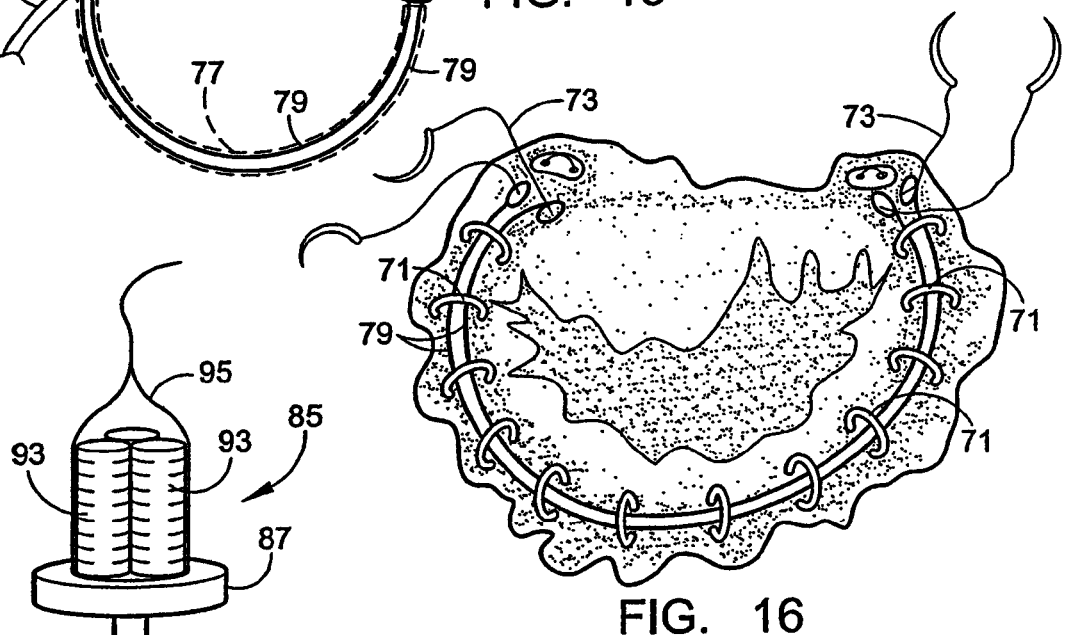
FIG. 16 is a perspective view of the valve of FIG. 14 with the partial annuloplasty band of FIG. 15 located in place and with the sheath removed to show a pair of flexible wires, the ends of which are ligated to the respective trigonal sutures.

Illustrated in FIGS. 14-16 is an alternative procedure that may be used to implant a partial annuloplasty ring, which procedure is shown as being carried out to reconfigure a mitral valve. A pattern of staples 71 or other suitable support is first placed in the valve tissue along a path extending from commissure to commissure. More specifically, the two trigons "T" of the valve are identified, and two double-armed 2.0 pledgetted sutures 73 are placed, as in FIG. 2, and pulled for retraction. The mitral ring is identified and if necessary is pulled with the help of a skin hook. Staples 71 are then placed radially around the annulus from commissure to commissure as illustrated in FIG. 14. Staples of the style of the staples 29 may be used. The two needles of the trigonal suture 73 on the left-hand side are then threaded through holes provided in ears 75 in a connector at each end of a sheathed wire system 77 which may include one or two or more wires 79 which will have sufficient flexibility to permit them to be routed through the pathway provided by the pattern of staples 71. The wires may be made of a metal alloy or of polymeric material, and they optionally may be of a shape-memory material, such as Nitinol. Their necessary length is determined by gauging the valve, and the wire system is constructed to provide points of attachment at the tail end, e.g. apertured ears 75, through which the two trigonal suture needles can be passed.

The leading end of the partial band system 77 is elongated to provide an introduction portion 81 at the end of the sheath which envelopes the right-hand end of the two-wire system and has a needle 83 threadably connected of its tip end. The needle 83 enables the routing of the wire system 77 between the bights of the staples 71 and the surface of the tissue in which the staples are implanted. Routing begins at the left-hand end and proceeds through the entire pathway to the opposite commissure. When the end of the wire system 77 protrudes through the last staple, the sheath portion of the system is removed to expose the pair of apertured ears 75 at the leading end and the pair of wires 79 that extend end-to-end and constitute the annuloplasty band. Once the trigonal anchoring sutures 73 are ligated to the attachment ears, the installation is complete. If the wires 79, which make up the wire system are of shape-memory material, they will then slowly assume the desired shape into which the valve is to be reconfigured, and some heating can be supplied, but should not likely be necessary. Once the heart has been closed, and the heart begins to beat on its own, the shape of the valve will steadily improve to an optimum configuration where it is fully competent.

Figure 17:
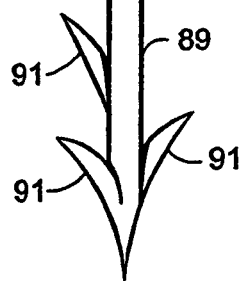
FIG. 17 is a perspective view of an anchor that can be used with an alternative system embodying various features of the invention.

Illustrated in FIGS. 17-22 is a further alternative procedure which obviates the need to employ a pair of pledgetted sutures for ligation at the trigona. Instead, two individual supports 85 are employed that can be quickly inserted into and anchored in the tissue precisely at each trigone and thereafter employed to mount the ends of an open annuloplasty ring of a type designed to permit some initial adjustment by the surgeon at the time of implantation so as to achieve the precise sizing desired. FIG. 17 shows an support 85 which may be employed for this purpose; it includes a circular base 87 and has an anchor section including a pointed, barbed shaft 89 which is designed to become affixed in the tissue. Once the two trigona have been identified with close precision, one of these supports is anchored at each trigone. The illustrated shaft 89 carries three barbs 91 extending outwardly therefrom and equiangularly spaced apart, e.g. by about 120°. The pointed shaft 89 protrudes into the tissue to the desired depth, with the undersurface of the circular base 87 tightly abutting the surface of the tissue, and the design of the barbs 91 is such to resist any upward withdrawal of the support. The support 85 includes an upstanding post section extending upward from the upper surface of the circular base 87 which is formed by three initially parallel rods 93 made of a shape-memory alloy, such as Nitinol. In their initial configuration, the rods 93 are parallel to the shaft and are surrounded by a restraining sleeve 95 which is removable as described hereinafter. Once the two supports 85 have been implanted anchored, the surgeon measures the distance about the valve annulus from one anchor along the path to the other anchor and selects the size of an open annuloplasty ring.

Figure 18:
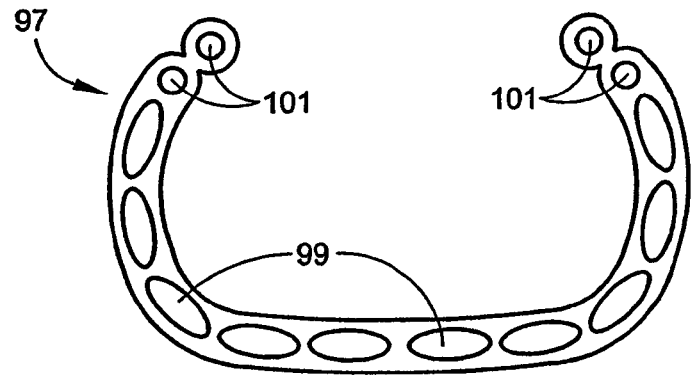
FIGS. 18 and 19 show two partial annuloplasty rings that may be employed as part of such system along with the anchor posts shown in FIG. 17.

Illustrated in FIG. 18 is a fenestrated ring 97 particularly designed for implantation with this implantation system. The partial annuloplasty ring 97 resembles that shown in FIG. 12, being made of similar metal, and a plurality of windows 99 run down its spine for its entire length. However, the ring has a pair of aligned circular holes 101 in each end which are sized so as to fit over the sleeve 95 which is restraining the three upstanding rods. The surgeon chooses one of the holes at each end for the initial installation and starts inserting staples along the ring using the sequential placement procedure described hereinbefore. After the A and B staples have been installed, the surgeon checks the fit, and if it is felt that the ring is too large, the second hole 101 on one end can be placed over the anchor and the checking repeated. In the unlikely instance that it would still be too large, a further adjustment can be made by moving the other end of the fenestrated ring 97 to the second hole 101. The remaining staples are inserted, and the restraining sleeves 95 are removed from the groups of posts at each anchor. Body temperature causes the posts 93 to assume a generally C-shape bending around and over the end sections of the fenestrated ring that form the perimeters of the holes 101 and securely fastening both ends to the tissue.

Figure 19:
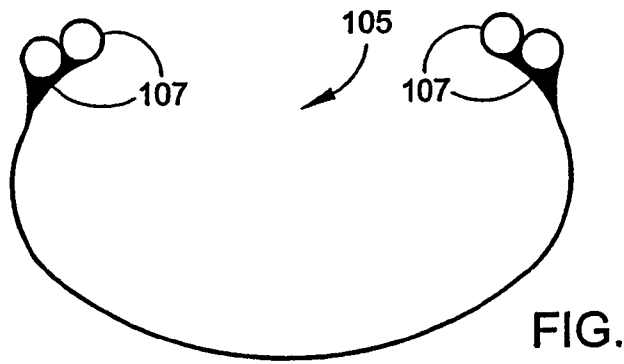
Figure 20:
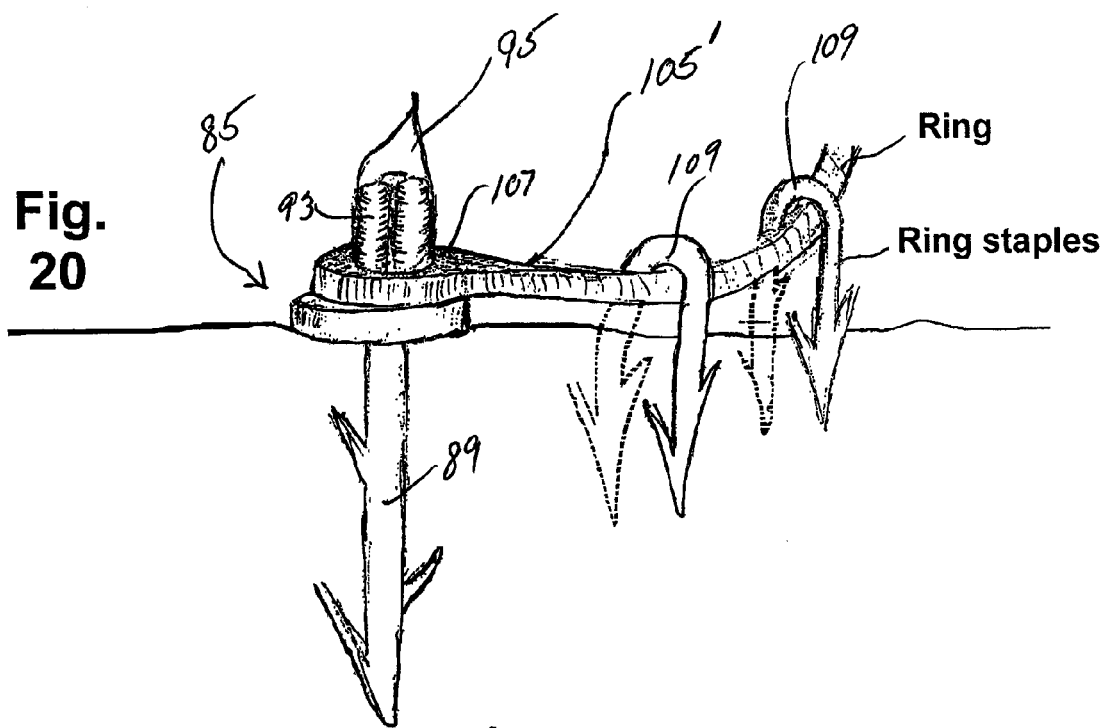
FIGS. 20 and 21 are schematic perspective views showing the installation of a system incorporating a wire annuloplasty ring similar to that illustrated in FIG. 19.
Figure 21:
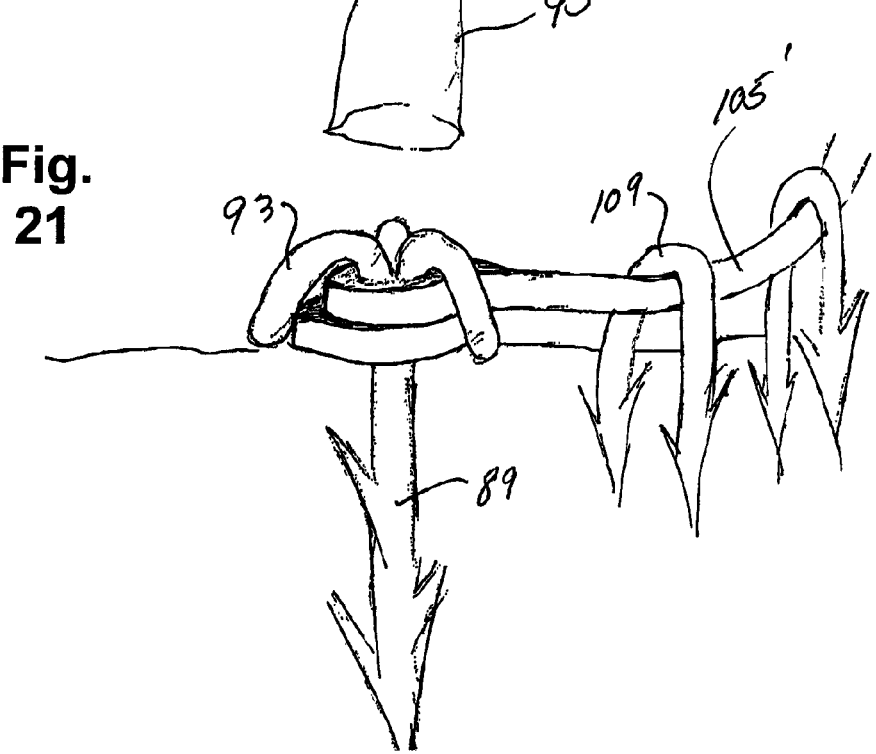

Illustrated in FIG. 19 is a wire ring-type annuloplasty ring 105 similar to the wire ring 67 described with respect to FIG. 11. The major difference is that apertured ears 107 at each end are axially aligned with the wire itself. Implantation of the ring is preferably carried out generally similarly to that just described; however, alternatively, staples could be initially implanted in the tissue to define the desired pathway and then one end of the wire ring threaded through the path, as previously described with regard to FIGS. 14-16. Again, once the two supports 85 have been anchored at the precise locations of the trigona, the surgeon makes the measurement to determine the length of the ring, and a suitable wire partial ring 105 is selected and installed, as depicted in FIG. 20. For simplicity purposes, an illustrated wire ring 105' having only a single apertured ear is shown; however, it should be understood that the preferred embodiments have two aligned apertured ears 107, as shown in FIG. 19, to permit adjustment. Once the wire ring is suitably aligned, barbed staples 109 are inserted at generally equal distances apart along the ring using the sequential placement procedure previously described. Once a predetermined number of staples 109 are in place, the surgeon checks the length, and if desired, shortening can be effected by repositioning one or both ends of the wire ring 105 to place the second aperture 107 from the end over the upstanding posts of the anchor 85. Thereafter, the restraining sleeve 95 is removed and the temperature causes the shape-memory alloy posts 93 to curl over the edges of the apertured ears 107, as schematically shown in FIG. 21, locking each ear to the upper surface of the base 87 of the support.

Figure 22:
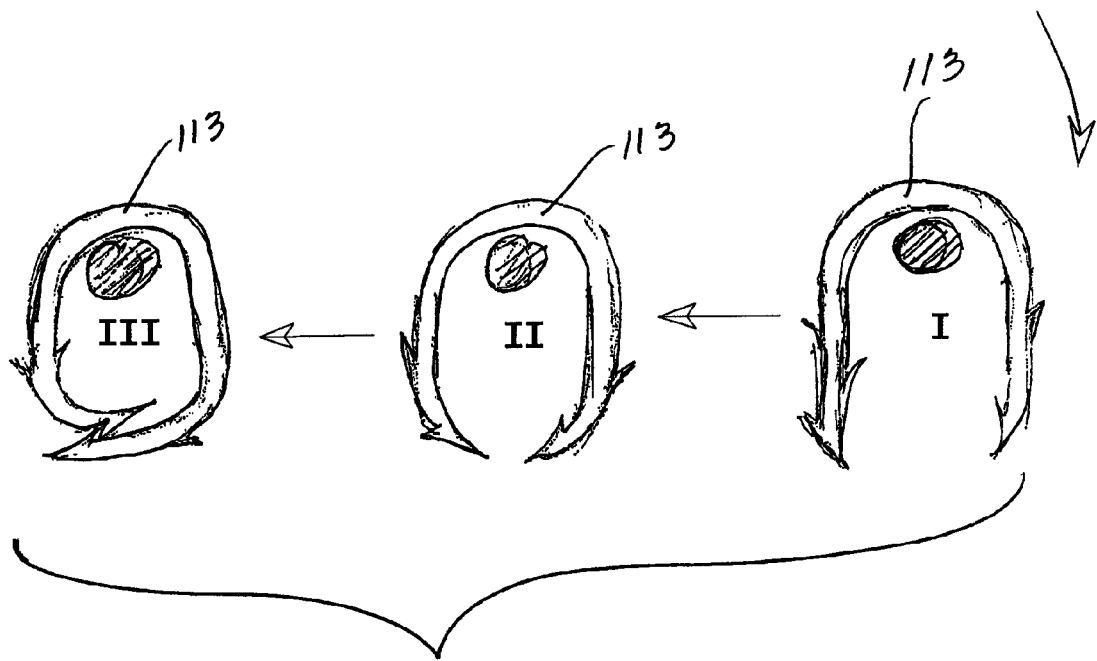
FIGS. 22 and 23 are perspective views illustrating the system depicted in FIG. 20 using an alternative shape-memory staple.
Figure 23:
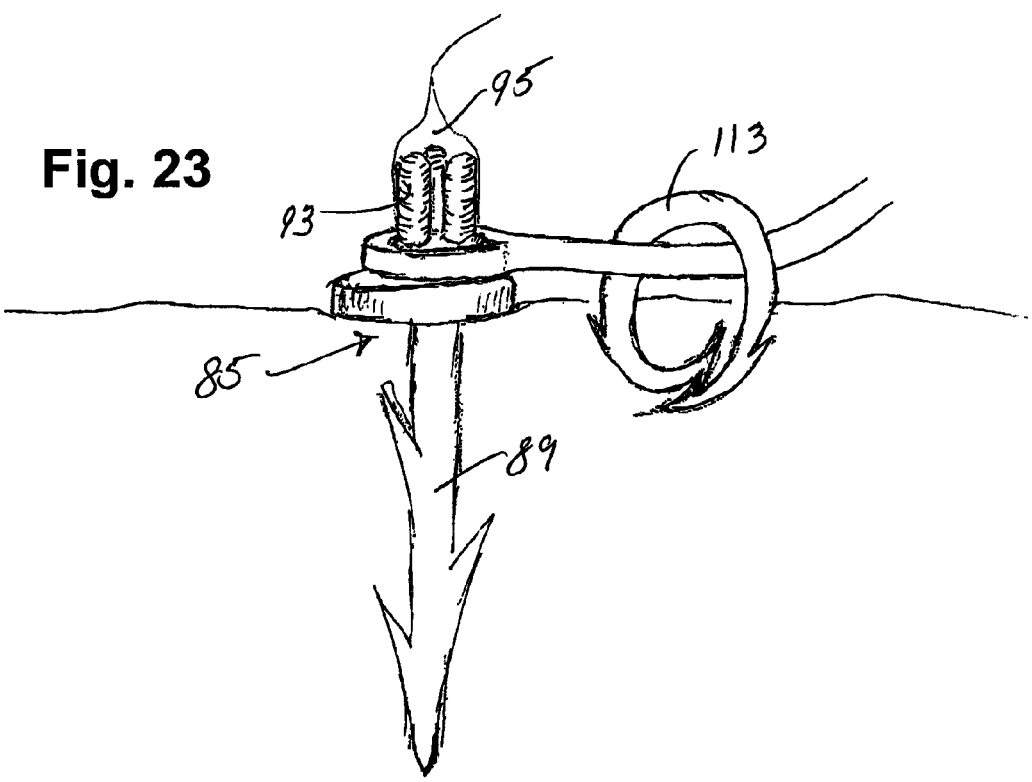

FIGS. 22 and 23 illustrate an alternative use of barbed staples 113 made of a shape-memory material such as Nitinol alloy. The staples 113, when implanted, have the U-shape depicted in FIG. 22 in the right-hand view. The shape-memory staples, upon warming to a temperature of the heart tissue, begin to slowly close as depicted in the middle view until they reach the closed configuration where the barbs interlock, as shown in the left-hand view and described hereinbefore. As depicted in FIG. 23, these shape-memory staples 113 thus securely fix a pathway for a wire ring, and once it is decided that either no adjustment to the length is necessary or once such adjustment is made by selecting a different one of the pair of apertured ears, the restraining sleeve 95 is removed so the three parallel posts 93 shown in FIG. 23 can then automatically curl radially outward to wrap around the edges of the respective apertured ear and assume the final orientation depicted in FIG. 21.

Instead of using an integral annuloplasty ring, it has been found that an alternative method can very effectively employ a series of supports which comprise linkers made of shape-memory material, such as Nitinol alloy, which will interconnect spaced-apart supports located along a desired pathway along a portion of the annulus of a patient's mitral or tricuspid valve so as to form a chain. The effective length of each linker decreases when they reach body temperature and causes the valve to assume the desired curvature at which the valve leaflets will perform effectively.

Figures 24, 25:
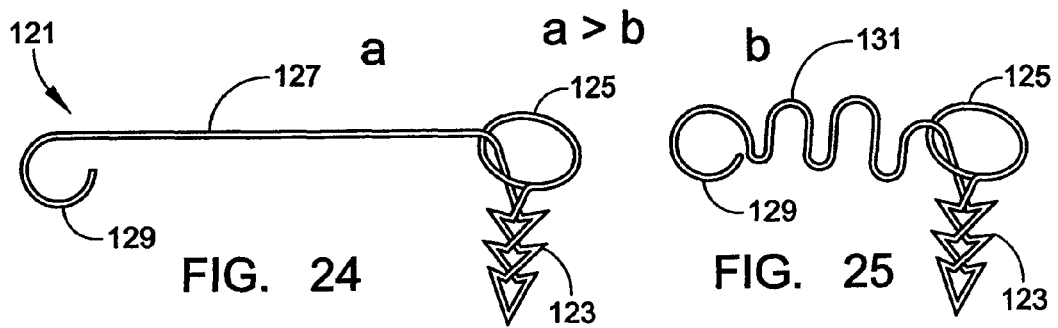
FIG. 24 is an elevation view, enlarged in size, of an implantable support having a linker arm made of shape-memory material.
FIG. 25 is a similar front elevation view of the support of FIG. 24 showing it after it has reached body temperature and reverted to its original undulating shape.

By effective length is meant the distance between the opposite ends of the linkers. Illustrated in FIG. 24 is a support 121 which has a depending anchor section 123 and an upstanding post section 125 which includes a circular portal or loop. A linker in the form of an arm 127 extends from an edge of the portal and is made of shape-memory material. The linker arm has the form of a stiff wire having engaging means at its end in the form of a hook 129. In the illustrated embodiment, the support 121 is formed from a single piece of wire alloy with the anchor sections 123 being formed as a plurality of barbs that radiate from a central core region. Alternatively, a shaft as previously described with respect to the supports 85 with a series of radial barbs could be used that is affixed to the shape-memory linker, and the portal could be a part of either the shaft or the arm.

Figure 26:
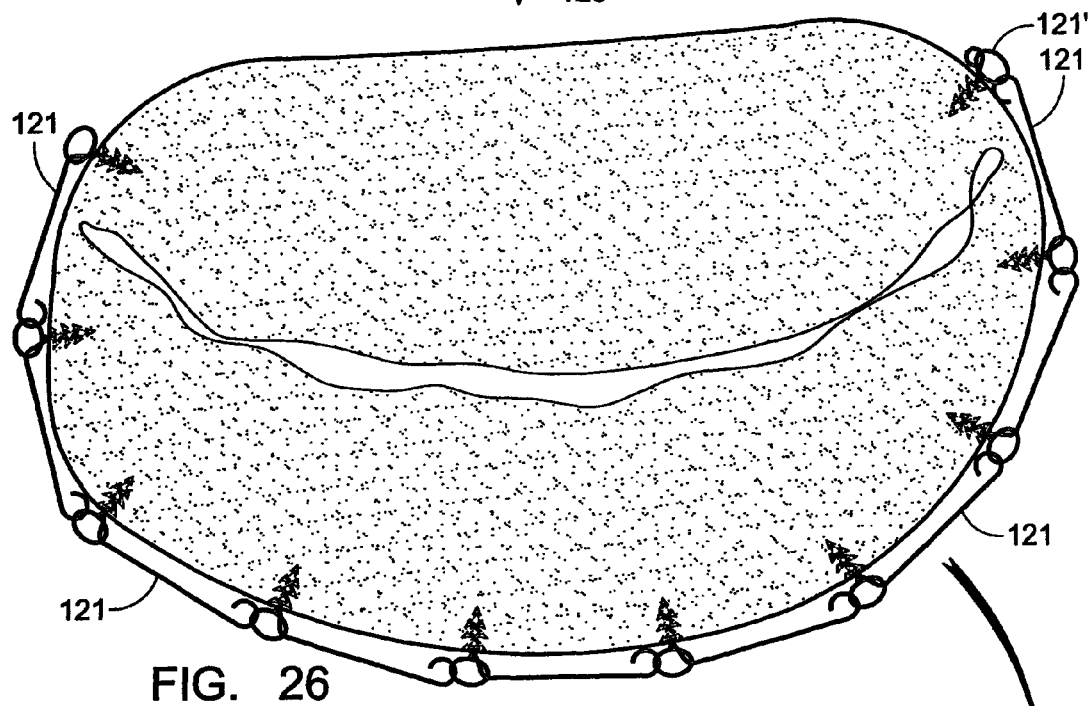
FIG. 26 is a view of a mitral valve, similar to that shown in FIG. 14, where a plurality of the linker arm supports of FIG. 24 have been implanted from commissure to commissure along a section of the native of the diseased mitral valve.

The surgeon who is reconfiguring the heart valve places a support 121j' that is devoid of a linker arm at one trigone, as illustrated in FIG. 26. A series of supports 121 are then implanted along the desired path that will provide the desired curvature of the valve so the leaflets will regain their effectiveness in blocking flow through the valve in the reverse direction. In each instance, the hook 129 at the end of the arm 127 of a support 121 is interengaged with the portal in the post section 125 of the last implanted support as it then has its anchor section 123 forced into the annulus tissue to implant it along the path to create the arrangement for a mitral valve as illustrated in FIG. 26. This results in a chain of interengaging linkers from support 121 to support 121 along the entire arcuate path selected to reconfigure the valve.

Figure 27:
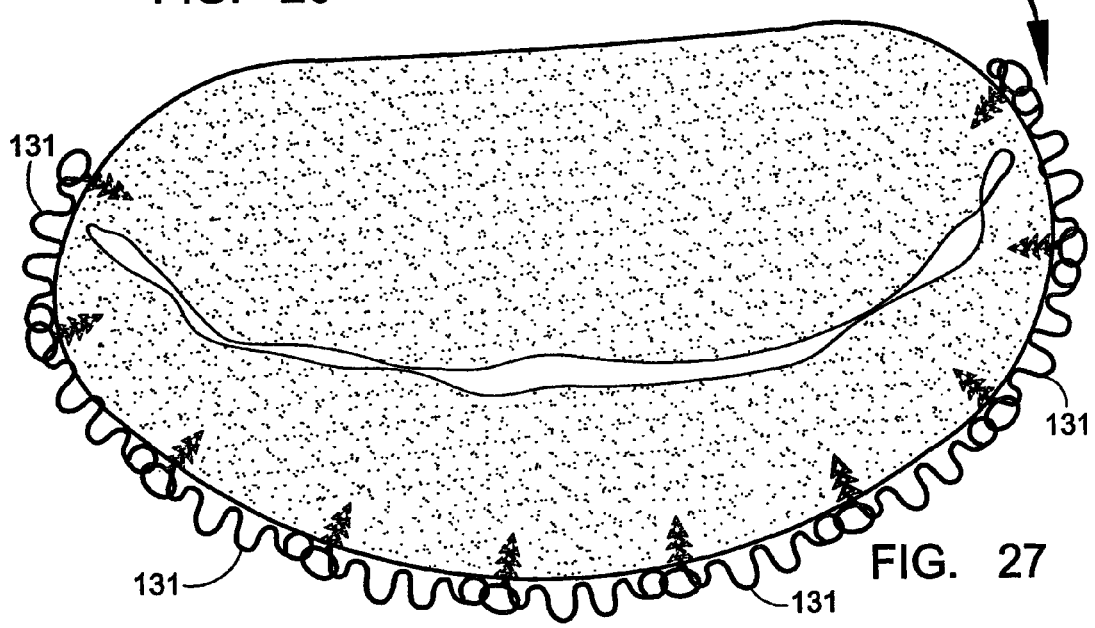
FIG. 27 is a view showing the implanted system of FIG. 26 after the individual linker arms have returned to their original shapes, decreasing the effective length of each arm and reconfiguring the shape of this section of the mitral valve.

As the shape-memory alloy material slowly reaches body temperature, the material returns to the original shape in which it was formed, which is shown in FIG. 25 as shape "b". More specifically, the straight arm 127 changes from its linear form (shape "a" in FIG. 24) when implanted to now have a series of bends or undulations 131, as depicted in FIG. 25; this shortens the effective length of each linker arm and causes the implanted supports 121 to be drawn closer to one another, thereby shortening the length of the arcuate chain and reducing this portion of the annular circumference to the desired dimensions calculated by the surgeon. At the same time, the hooks 129, that were initially interengaged through the portals, close into circular loops thus securing the interengagement between the end of the linker arm and the next adjacent support, as also shown in FIGS. 25 and 27. Although the path along which these supports are located preferably extends from about one commissure to the opposite commissure, there may be instances where the use of supports extending a substantial distance along such path may be adequate. Usually such a substantial distance will constitute at least about 50 or 60% of the total distance, and preferably at least about 80%.

Shown in FIG. 28 is an alternative embodiment of a support 135 which includes a similar anchor section 137 (but which could also be a barbed shaft as shown in FIG. 17) wherein the upstanding section includes a base 139 in the form a cross or X-shape to which are affixed a pair of parallel arms 141 which are made of stiff, shape-memory alloy material of wire form. The arms are formed with a pair of hook sections 143, the ends of which are joined by a crossbar 145, forming a first interconnector. The opposite ends of the two arms 141 are also formed as hook sections 147 the termini of which are affixed to a crossbar 149 (which may be integral therewith) to form a second interconnector. The crossbars 145 and 149 differ slightly in size so that the respective hook sections are spaced apart slightly differently so that the smaller interconnector at one end of a support 135 can be fit between the hook sections of the larger interconnector and thus juxtaposed with the interconnector at the opposite end of the next adjacent support in the path so that they interengage with the smaller interconnector looping around the crossbar of the larger.

When the implanted supports 135 reach body temperature, the shape-memory alloy causes the hook sections 143 and 147 to change shape to form closed loops. At about the same time or preferably slightly thereafter, the arms 141 effectively shorten by the creation of undulating bends 151, as seen in FIG. 29. As a result, the longer of the two crossbars 145, 149 is now encircled by the smaller interconnector at the other end of the next adjacent support 135, locking the two in interengagement. It can thus be seen that for a chain of these supports 135 wherein the pair of arms 141 on each support has decreased in effective length results in a reconfiguration of the curvature of the valve in the same manner as that illustrated in FIG. 27.

Although the arrangement of the support that is illustrated in FIGS. 28 and 29 locates the base 139 near one end of the linker formed by the pair of arms 141, it should be understood that, if desired, a support 152 may have a base 153, from which the anchor section 154 depends, located generally centrally of the ends of the pair of arms 155 and hook sections 157 which both bend upward, as shown in FIGS. 30 and 31, but include crossbars 145, 149 of different lengths. In this instance, the arms 155, in both regions between the base 153 and the hook sections 157, would form undulations 159 flanking the central base section. FIG. 31 shows the form which such an alternative support 152 would have at the time at which it would be implanted, and FIG. 32 shows a section of a chain of such interconnected supports 152 after the arms 155 have formed a series of undulations 159. Although the undulations 159 are shown as lying in a vertical plane, the support may alternatively be formed so that they lie essentially in a horizontal plane parallel to the surface of the valve tissue.

FIGS. 14A-14C illustrate an alternative embodiment of a method for reconfiguring an atrioventricular heart valve to that shown in FIGS. 14, 15 and 16. Instead employing a flexible wire of shape-memory alloy material that is threaded through the staples, a similar series of staples 71 are implanted along the desired path as before, and in addition, two additional staples are implanted near the commissures where the sutures were previously ligated. Adjacent pairs of staples 71 are then serially interconnected by linkers 161 of stiff wire form which embody an arm 163 and a pair of hooked ends 165. Each linker 161 is hooked at one end about one of the implanted staples 71 and then the opposite end of the linker is hooked about the next adjacent staple along the path until the entire chain of staples from commissure to commissure has been put in place. The staples 71 are of shape-memory alloy material, such as described in FIG. 22 for example; they preferably will have already achieved a secure or interlocked configuration before the linkers are attached. As the temperature of the linkers arises to the body temperature, the hook ends 165 of each of the linkers deform into essentially closed loops, and the arms 163 of the supports return to their original configuration to present a series of undulations 167 which effectively shorten the length the linkers, pulling the adjacent pairs of staples toward one another and reconfiguring the valve to assume the desired curvature where the leaflets will effectively close to prevent blood flow in the opposite direction during the pumping cycle of the heart.

These staples and various of the other supports illustrated herein may be delivered by a special gun having a size such that it can introduced through a cardiac catheter which enters from a patient's groin, and following the implantation of the staples in this manner, the simple linkers 161 can be similarly placed by the surgeon non-invasively through such a cardiac catheter. The placement of supports similar to the supports 121 non-invasively is described and shown in FIGS. 40-43 hereinafter.

FIG. 33 illustrates the elements of another system that can be used to reconfigure an atrioventricular heart valve, alternative to that illustrated in FIGS. 28 and 29 and that illustrated in FIGS. 30-32. The system employs a central support member 171 and separate linkers 173. The central support 171 includes an anchor section 175 and a base 177 from which the anchor section depends. The base is formed with a pair of slots 179 that define crossbars 181 adjacent opposite edges of the base.

The linkers are made in wire form and include a pair of generally parallel arms 183 which end in hook sections 185. At each of the two ends of the linkers 173, the parallel arms 183 are interconnected by a pair of crossbars 187a and 187b. The crossbars stabilize the ends of the linkers 183.

During the implantation, the surgeon first implants a series of spaced apart support members 171 along the desired path as explained hereinbefore. Each of the anchor sections 175 is forced into the annulus tissue, and it is retained in place by barbs 189 formed as a part thereof. As the support members 171 gradually warm to body temperature, the anchor section 175 of shape-memory material begins to slowly change shape. It is formed as a pair of split legs 191, and as seen in FIG. 34, the ends of these legs slowly spread radially in opposite directions thus further securing the barbed elements within the annulus tissue. The linkers 173 are then installed between adjacent central supports 171 by sequentially hooking the hook ends 185 of the arms through the slots 179 so they partially wrap around the crossbars 181 of the base 171; this configuration is shown in FIG. 34. FIG. 35 shows the next step where, upon warming, the hook ends 185 deform into essentially closed loops which effectively encircle each of the crossbars 181, completely securing the interengagements. At about the same time or preferably shortly thereafter, the arms 183 have warmed sufficiently to return to their original shapes in the form of a series of undulations or bends 193, effectively shortening the length of the linkers and pulling the central supports toward one another to create the desired curvature of the heart valve. This final arrangement is schematically shown in FIG. 36 without illustrating the associated heart valve, as was shown with various of the earlier systems.

Illustrated in FIG. 37 is an alternative embodiment of a central support 197 that might be employed instead of the central support 171 illustrated in FIG. 33. This support may employ a similar base section; it employs an anchor section 199 which is split into four barbed legs 201 which, upon warming, bend radially outward at their free ends, generally at 90° angles to one another, to take the implanted form shown in FIG. 37.

FIG. 38 depicts yet another alternative embodiment of a central support 203 which maybe formed with either of the previously described anchor sections but which employs a base section 205 of wire form generally similar to that shown in FIGS. 28 and 29. The base includes a pair of hooked interconnectors 207 which include crossbars 209 that function the same manner as the crossbars 181 described just above.

FIG. 39 depicts an alternative embodiment of a linker 211 shown generally in the form it would take following implantation. It has a pair of hooked ends 213 generally similar to the hooked ends 185 which include crossbars; however, instead of having a pair of parallel arms, a single arm 215 is employed which, upon warming to body temperature, forms a series of undulations 217 which effectively shorten its length.

Various of the previously described systems may be employed in non-invasive narrowing of the mitral valve, particularly in a patient suffering congestive heart failure (CHF). The system would permit non-invasive means being employed to actually repair the valve by entering the artery in the groin region using delivery-catheter based technology. Shown schematically in FIG. 40 is a catheter 221 of the guidable variety well known in this art which can be employed to deliver a plurality of supports 223, such as supports as generally shown in FIG. 24 that are preferably, but not necessarily, linked together in a chain of the desired length. The catheter 221 may be made in accordance with any of the commercially available designs for guidance and delivery, such as those found in U.S. Pat. Nos. 6,723,082; 6,663,666; 6,482,221; and 6,572,643. Generally these catheters 221 will have as many as four steering wires 225 arranged for example at annular locations at 90° to one another, as shown schematically in a cross-sectional view in FIG. 41.

As well known in this art, these catheters 221 would carry the electronic and space sensing elements to facilitate the manipulation and operation of the delivery catheter. For example, the end of the catheter would likely be provided with the electro-magnetic sensors 227 which would allow the operator to precisely identify the location of the tip of the catheter within the body of the patient spatially on X, Y and Z axes, as determined from a platform on which the patient would be lying. In addition to knowing the spatial location of the catheter tip, ultrasonic sensors/transducers would be likely provided that would show the relative position of the tip with reference to the contour of the heart tissue and with an electrode using electrical mapping of the mitral annular region (here the interior wall of the left ventricle) so that, in this instance, the cardiologist would be able to precisely position the tip of the catheter along the region of the circumference of the mitral valve that is to be shortened through this surgical procedure.

The catheter 221 would be inserted from the patient's groin, retrograde into the aorta and then through the aortic valve 231 into the left ventricle as depicted schematically in FIG. 42. Suitable guidance systems of this type are available and are shown for example in U.S. Pat. No. 6,322,548 where a catheter is similarly delivered; once in place within the left ventricle of the heart, it is used to deploy a sharp or needle through an injection is made. Such an operation is depicted in FIGS. 9 through 11 of this patent, where wire loops made of Nitinol are used to serve as penetration limiters and wherein, once the operator has determined that the device is in the correct position, the distal tip of the needle is extended into the heart tissue.

In the system illustrated herein, the first support 223 would be projected through the open end of the delivery catheter with its pointed anchor portion 223 positioned against the heart tissue at the location where it is desired that shortening of the valve circumference should begin. The distal end of the catheter carries an inserter 235 which is designed to grasp the support 223 in the region above the anchor and forcefully insert it into the heart tissue. After the initial support 223 has been implanted, the catheter 221 is manipulated so as to position the next support 223 at its desired location, with an arm 237 of the support interconnecting the two. Although totally separate supports could be employed that would be linked together using any of the systems previously described herein, the operation may be simplified if the supports are already interlinked as a chain when they are loaded into the delivery catheter 221. With the second support 223 in position, it is then also forcefully inserted into the tissue by activating the inserter 235. The operation is repeated until the chain of the desired length selected by the surgeon has been placed in the desired location.

Once the installation has been complete, the delivery catheter 221 is withdrawn, and the chain of interlinked supports 223 would appear as shown in FIG. 43. If the shape-memory material is of the Nitinol alloy type, the arms 127 automatically shorten upon warming to body temperature, and the reduction in the circumference of the mitral valve occurs. If some other type of shape-memory material were to be employed, the application of energy e.g., selected electrical current, UV, ultrasound or the like, might be employed to cause the material to regain its initial shape where the arms will have shortened in effective length via the creation of a plurality of undulations, as described hereinbefore.

Figure 44:
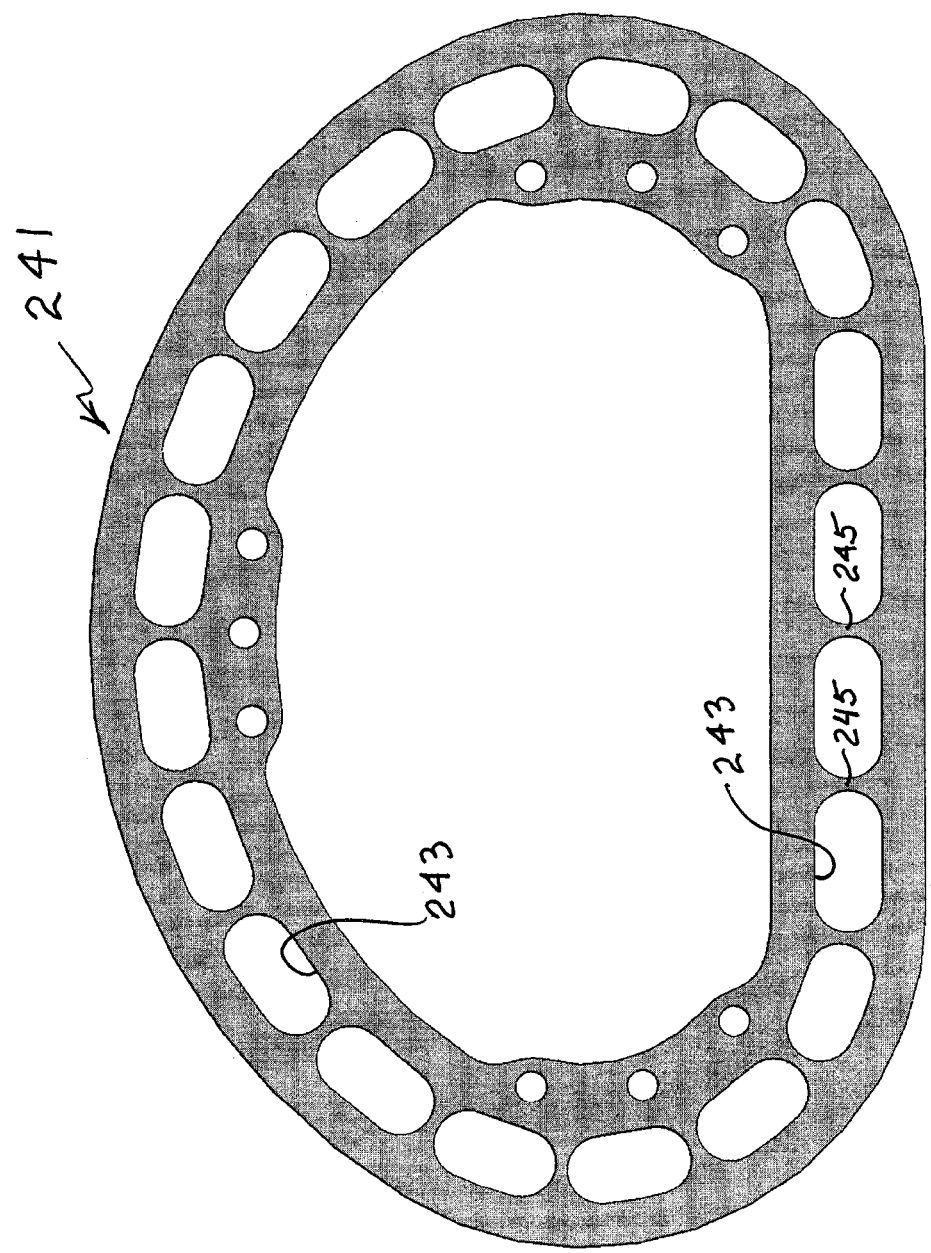
FIG. 44 is a plan view of a fenestrated complete annuloplasty ring generally similar to that shown in FIG. 12.
Figure 45:
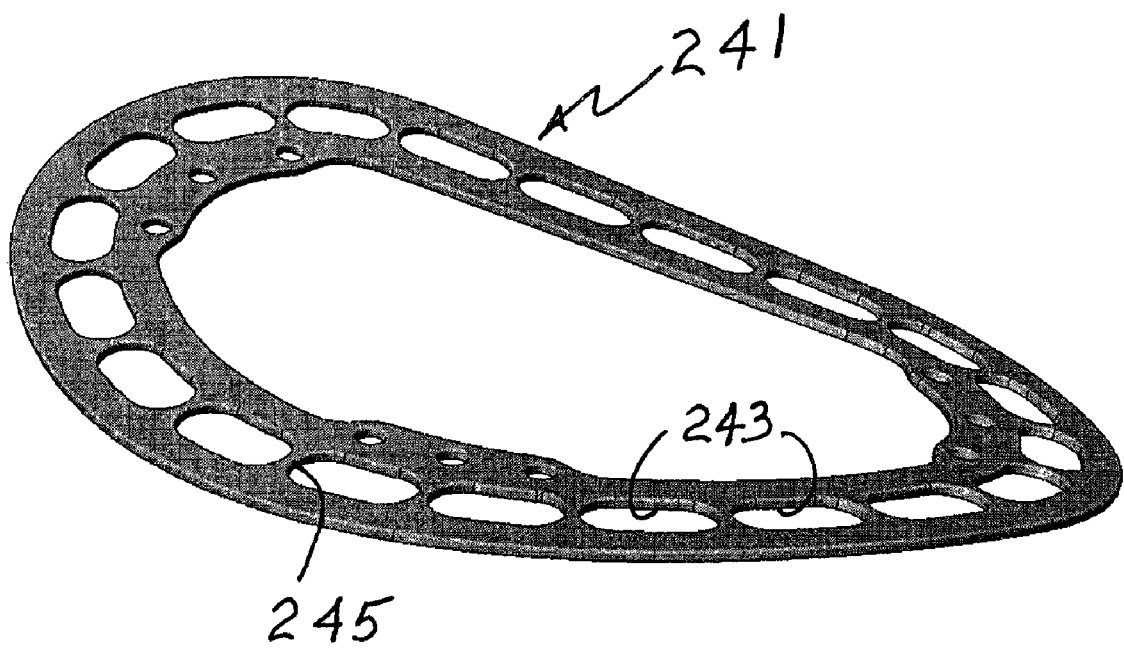
FIG. 45 is a perspective view of the ring of FIG. 45 shown as it might flex out of the planar orientation.

FIG. 44 shows a fenestrated annuloplasty ring 241 similar to that shown in FIGS. 12 and 13 but in the form of a complete ring of generally D-shape. It similarly has a plurality of elongated windows 243 that are uniformly spaced apart along it entire length. It could likewise be made of a suitable metal alloy and then secured to the heart valve tissue, as described with respect to FIGS. 12 and 13, by the use of appropriate staples. Staples could be installed so as to straddle the outer edge of the ring as illustrated in FIG. 13 or could be installed so as to straddle the bars 245 which separate adjacent windows 243 with one leg of the staple in each such window. As indicated hereinbefore, because the cross-sectional area of the leg of the staple is such that it occupies only a few percent of the cross-sectional area of the window 243, some movement will be permitted between the heart valve tissue and the juxtaposed surface of the ring 241, thus allowing subtle shifting of the valve tissue with respect to the ring, which permits the shape of the valve to steadily improve to an optimum configuration where its natural leaflets achieve better coaptation. However, the annuloplasty ring 241 can be made from a material which is flexible so that it will bend in the plane of the ring so as to follow the natural movement of the surface of the heart valve tissue as depicted in FIG. 45, but which is substantially inextensible so that it will not significantly stretch from its shape as seen in FIG. 44. Such a ring 241 may be made from any suitable biocompatible polymeric material exhibiting such physical properties. For example, it may be made from medical grade Gore-Tex (expanded PTE), which is commonly employed for many different medical purposes. A ring might also be made of autologous material for a particular patient, as by removing pericardium from the patient, shaping a ring therefrom and treating it with glutaraldehyde or the like in order to provide sufficient strength and render it resistant to elongation by such fixation while still remaining flexible. Of course, animal pericardium could likewise be used to fashion fenestrated rings of this general design. The potential advantage of such a pliable ring can be better visualized in reference to FIG. 45 where the ring is shown in a bent orientation to which it might flex during the normal beating of the heart.

Figure 46:
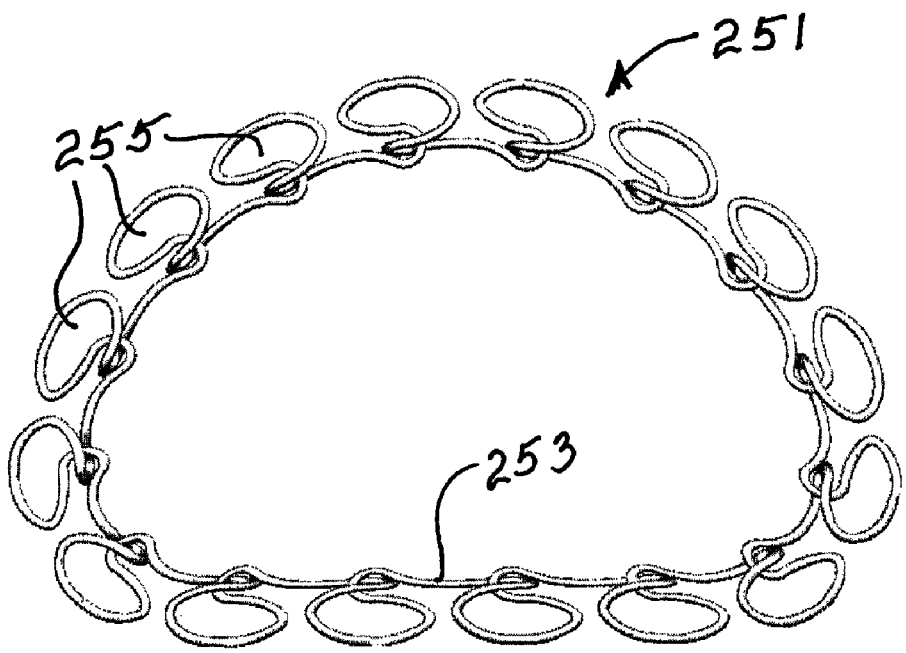
FIG. 46 is a plan view of another embodiment of a fenestrated or windowed annuloplasty ring formed from wire material of circular cross section having a generally D-shape.

Illustrated in FIG. 46 is an alternative embodiment of a planar fenestrated annuloplasty ring 251 that has a D-shape such as might be used for the repair of a deficient mitral valve. By planar is meant that the ring 251 is flat such that it would occupy a plane having a thickness equal to about 5 to 10 times the diameter of the wire. It is formed of a wire material of circular cross section so as to create a complete wire ring 253 with a series of spaced apart windows 255 along its entire length provided by closed loops of wire. Its properties will depend upon the material used; for example, if formed from a very stiff wire, it could be a relatively rigid ring, as compared to the heart valve tissue. However, this construction would more likely form a polymeric or metal alloy wire material into a pliable ring; such a ring, while being inextensible, would flex in its plane in much the same fashion as shown in FIG. 45 for the ring 241. The windows 255 in the ring illustrated in FIG. 46 are created by fashioning a loop and twisting the wire to form a completely closed window of desired elongated shape. Adjacent windows are preferably located so that a staple could straddle two windows with a leg in each without touching either loop.

Figure 47:
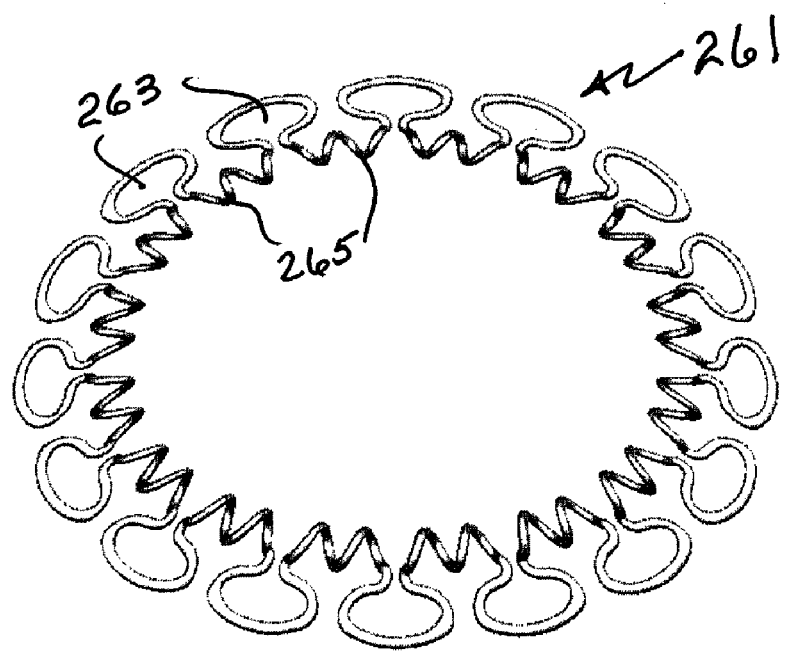
FIG. 47 is a view of still another alternative embodiment of a fenestrated ring formed of wire material which is shown in an initial circular shape.

FIG. 47 shows an alternative version of a ring 261 where the wire form material is shaped to provide a series of windows 263 in the form of loops that are slightly open at the radial inner edges thereof where they connect to sinuous sections 265 of the wire that form a complete circle. The ring 261 is shown in its initial circular form. It is anticipated that a surgeon would custom shape it to an appropriate D-shape before delivery to the patient's heart; thus, the material chosen for construction would preferably be one that would take a memory set as chosen by the surgeon so that it would return to such planar configuration between flexings.

Figure 48:
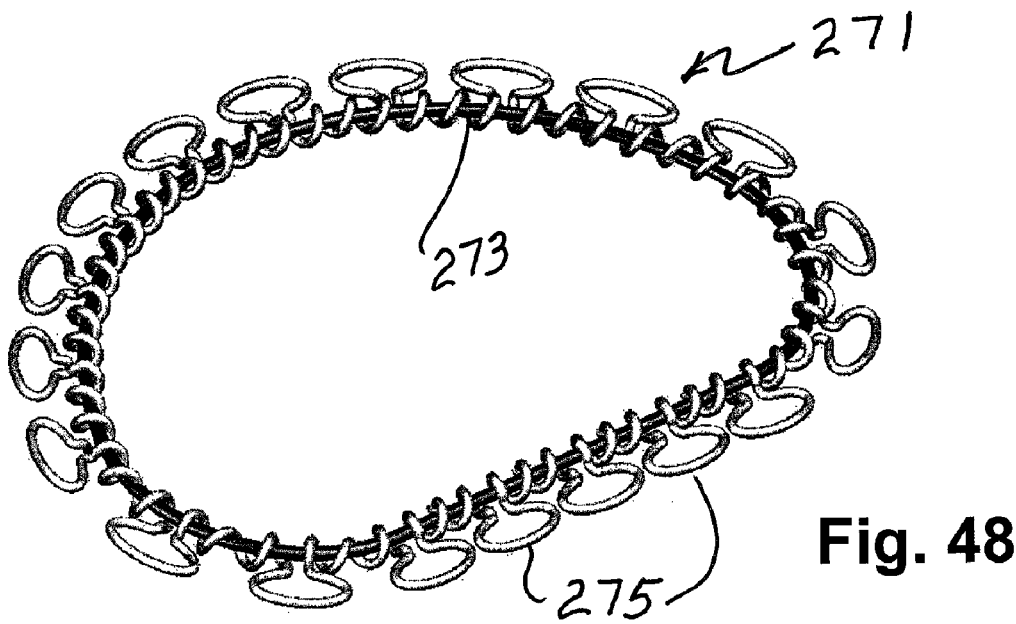
FIG. 48 is a perspective view of a further embodiment of a fenestrated annuloplasty ring generally similar to the ring of FIG. 47, which includes a stabilizing core element.

Shown in FIG. 48 is still another alternative embodiment of an annuloplasty ring 271 which has the general construction of that shown in FIG. 47 but includes a central D-shaped core element 273. The presence of the core element 273 adds some additional stability to the flexible annuloplasty ring 271, and as can be seen, its windows 275 are closed on their radially inward side by the section of the core element so they are completely closed. The core element 273, as with respect to the circular cross section wire material from which the remainder of the ring 271 is formed, is likewise selected so as to be inextensible but to allow flexing in the plane of the ring to allow bent configurations to be achieved generally as depicted in FIG. 45.

Figure 49:
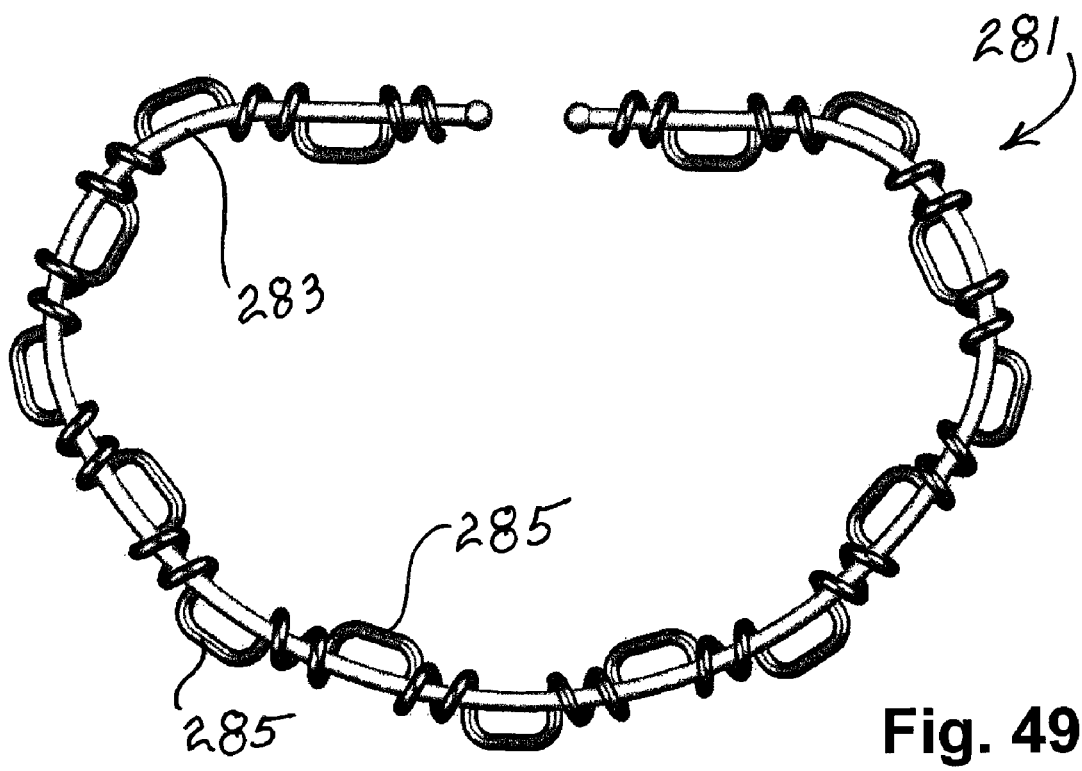
FIG. 49 is a view of another embodiment of a fenestrated partial annuloplasty ring of D-shape, having a core element similar to that shown in FIG. 48.

One still further embodiment of a partial annuloplasty ring 281 is shown in FIG. 49. It again is shown as having a D-shape and incorporates a partial linear core element 283 about which there is wrapped the wire form material that creates windows 285 of the fenestrated partial ring. Because the windows 285 are formed so that they alternate with respect to the radially inner and radially outer borders of the core element 283, all the staples would of course reside with only one leg in a window.

Oftentimes it is deemed feasible to avoid replacement of a valve that has become incompetent by implantation of an annuloplasty ring, and this operation has now been greatly facilitated via the use of the previously described stapling procedures. By reducing the time of such phase of an operation by 50% or more, side effects of being an artificial life support are greatly lessened, and full recovery is significantly hastened.

Although the invention has been described with regard to certain preferred embodiments, it should be understood that various changes and modifications that would be obvious to one having the ordinary skill in this art may be made without departing from the scope of the invention which is defined in the claims appended hereto. For example, although only certain specific staple shapes have been illustrated, it should be understood that a wide variety of staples, made optionally of shape-material, may be employed as the surgical stapling has become a well developed art. There are commercially available a number of custom designable staplers which can be employed to anchor annuloplasty rings while working at a distance of 25-35 centimeters from the annulus of a mitral valve. In the supports that use linkers in the form of pairs of generally parallel arms, the hook sections at each end at the respective ends of the arms may be arranged in varying orientations. Although it may be preferred that both hook sections curve upward from the arms with respect to the heart valve tissue against which the arms will be generally juxtaposed as depicted in FIGS. 30-32, it should be understood that, depending upon the size and length of the support and the orientation of the pair of arms, one or both of the hook sections could be formed to curve downward as shown in FIG. 28 to perhaps facilitate interengagement. It should likewise be understood that although different types of barbed ends of staples and anchors have been described with respect to different of the embodiments, essentially any of the individual arrangements can be substituted for those specifically described with regard to a specific embodiment when felt desired for a particular application. For example, any of the staples or the anchors could be constructed so as to be formed of a shape-memory alloy material that would deform after implantation into 2, 3, 4 or more spreading legs. The disclosures of all U.S. patents mentioned hereinbefore are expressly incorporated herein by reference.

Particular features of the invention are emphasized in the claims that follow.

The invention claimed is:

1. A system for reconfiguring an atrioventricular heart valve, which system comprises
a partial or complete fenestrated annuloplasty ring having a size and shape proportioned to reconfigure a heart valve of a patient that has become in some way incompetent, and a plurality of spaced-apart windows along the length of the ring, and
a plurality of staples having pairs of legs that are each sized to occupy only a minor portion of the area of one window when passed therethrough to be implanted in the heart valve tissue at spaced locations along the length of the ring and thus secure the ring to the heart valve tissue bordering the valve annulus in a manner that permits relative movement between said staples and said ring, whereby a patient's heart valve can be reconfigured in a manner that does not deter subtle shifting of the native valve as so to conform the annulus to said ring so the shape of the valve annulus will steadily improve to an optimum configuration where its natural leaflets achieve better coaptation.

2. The system according to claim 1 wherein said staples are made of a shape-memory material and wherein said legs have free ends which change shape to assume a secure angular orientation to the major length thereof following implantation in the tissue of a patient.

3. The system according to claim 1 wherein said staple legs have free ends that form an interlocking orientation following implantation.

4. The system according to claim 1 wherein said annuloplasty fenestrated ring has a plurality of spaced-apart elongated windows which are regularly spaced along the length thereof.

5. The system according to claim 4 wherein the legs of said staples are spaced apart a greater distance than the distance between two adjacent said windows.

6. The system according to claim 1 wherein said ring is planar in shape and made of material that is inextensible but flexible so that said ring will bend in the plane thereof.

7. The system according to claim 6 wherein said ring is formed of wire of circular cross section that is shaped to create a ring including a plurality of loops that provide said windows.

8. The system according to claim 7 wherein said loops are twisted to form closed windows.

9. The system according to claim 7 wherein said wire is bent about a linear core element which adds stability to the ring.

10. The system according to claim 9 wherein said wire is formed to create open loops which are closed by said core element.

* * * * *